US007241899B2

(12) United States Patent
Benigni et al.

(10) Patent No.: US 7,241,899 B2
(45) Date of Patent: Jul. 10, 2007

(54) METHODS FOR THE PREPARATION, ISOLATION AND PURIFICATION OF EPOTHILONE B, AND X-RAY CRYSTAL STRUCTURES OF EPOTHILONE B

(75) Inventors: Daniel A. Benigni, Skaneateles, NY (US); Jack Z. Gougoutas, Princeton, NJ (US); John D. DiMarco, East Brunswick, NJ (US)

(73) Assignee: Bristol-Myers Squibb Company, Princeton, NY (US)

( * ) Notice: Subject to any disclaimer, the term of this patent is extended or adjusted under 35 U.S.C. 154(b) by 169 days.

(21) Appl. No.: 10/805,724

(22) Filed: Mar. 22, 2004

(65) Prior Publication Data

US 2006/0135474 A1 Jun. 22, 2006

Related U.S. Application Data

(62) Division of application No. 10/668,032, filed on Sep. 22, 2003.

(60) Provisional application No. 60/412,994, filed on Sep. 23, 2002.

(51) Int. Cl.
*A61K 31/724* (2006.01)
*C12P 17/14* (2006.01)
*C07D 417/02* (2006.01)

(52) U.S. Cl. ............... 548/181; 435/119; 435/120; 514/58; 514/83; 514/365; 514/450; 548/203; 548/204

(58) Field of Classification Search ............ 548/181, 548/203, 204; 435/119, 120; 514/58, 83, 514/365, 450
See application file for complete search history.

(56) References Cited

U.S. PATENT DOCUMENTS

| 6,194,181 | B1 | 2/2001 | Hofmann et al. |
| 6,204,388 | B1 | 3/2001 | Danishefsky et al. |
| 6,211,412 | B1 | 4/2001 | Georg et al. |
| 6,242,469 | B1 | 6/2001 | Danishefsky et al. |
| 6,316,630 | B1 | 11/2001 | Danishefsky et al. |
| 6,369,234 | B1 | 4/2002 | Danishefsky et al. |
| 6,380,227 | B1 | 4/2002 | Mutz |
| 6,613,912 | B2 | 9/2003 | Hoefle et al. |
| 2004/0132146 | A1* | 7/2004 | Benigni et al. ............ 435/120 |

FOREIGN PATENT DOCUMENTS

| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/02514 | 1/1999 |
| WO | 99/03848 | 1/1999 |
| WO | 99/07692 | 2/1999 |
| WO | 99/27890 | 6/1999 |
| WO | 99/39694 | 8/1999 |
| WO | 99/42602 | 8/1999 |
| WO | 99/43320 | 9/1999 |
| WO | 99/43653 | 9/1999 |
| WO | 99/54319 | 10/1999 |
| WO | 99/67252 | 12/1999 |
| WO | 00/00485 | 1/2000 |
| WO | 00/31247 | 6/2000 |
| WO | 00/37473 | 6/2000 |
| WO | 00/49021 | 8/2000 |
| WO | 00/66589 | 11/2000 |
| WO | WO 00/71521 | 11/2000 |
| WO | WO 02/46196 | 6/2002 |
| WO | WO 03/070170 | 8/2003 |

OTHER PUBLICATIONS

U.S. Appl. No. 08/856,533, filed May 14, 1997, Nicolaou, K., et al.
U.S. Appl. No. 08/923,869, filed Sep. 4, 1997, Nicolaou, K., et al.
U.S. Appl. No. 60/032,864, filed Dec. 13, 1996, Nicolaou, K., et al.
Balog, A., et al., "Total Synthesis of (−)-Epothilone A", *Angew. Chem. Int. Ed. Engl.*, vol. 35, No. 23/24, 2801-2803 (1996).
Bertini, F., et al., "Alkenes from Epoxides by Reductive Elimination with Magnesium Bromide-Magnesium Amalgam", *Chem. Commun.*, 144 (1970).
Bollag, D.M., et al., "Epothilones, A New Class of Microtubule-stabilizing Agents with a Taxol-like Mechanism of Action", *Cancer Res.* 55, No. 11, 2325-2333 (1995).
Fujisawa, T., et al., "Deoxygenation of Epoxides to Olefins with $FeCl_3$—n-BuLi System", *Chem. Lett.*, 883-886 (1974).

(Continued)

*Primary Examiner*—Herbert J. Lilling
(74) *Attorney, Agent, or Firm*—Gary D. Greenblatt

(57) ABSTRACT

The present invention relates to improved methods for the production, isolation and purification of epothilone B. These methods include, for example, a fermentation process for the production of epothilone B, isolation via adsorption onto a resin, and subsequent purification.

9 Claims, 16 Drawing Sheets

OTHER PUBLICATIONS

Fujiwara, Y., et al., "Reductive Coupling of Carbonyl Compounds to Olefins by Tungsten Hexachloride-Lithium Aluminum Hydride and Some Tungsten and Molybdenum Carbonyls", *J. Org. Chem.*, vol. 43, No. 12, 2477-2479 (1978).

Gladysz, J. A., et al., "Deoxygenation of Epoxides by Metal Atom Cocondensation", *J. Org. Chem.*, vol. 41, No. 22, 3647-3648 (1976).

Hofle, G., et al., "Epothilone A and B—Novel 16-Membered Macrolides with Cytotoxic Activity: Isolation, Crystal Structure, and Conformation in Solution", *Angew. Chem. Int. Ed. Engl.*, vol. 35, No. 13/14, 1567-1569 (1996).

Hofle, G., et al., "N-Oxidation of Epothilone A-C and O-Acyl Rearrangement to C-19 and C-21 -Substituted Epothilones", *Angew. Chem. Int. Ed.*, vol. 38, No. 13/14. 1971-1974 (1999).

Inokuchi, T., et al., "Opening of Epoxides to Olefins or Halohydrins with Vanadium(II)-Tetrahydrofuran or Vanadium(III)-Tetrahydrofuran Complexes", *Synlett*, No. 6, 510-512 (1992).

Kowalski. R. J., et al., "Activities of the Microtubule-stabilizing Agnets Epothilones A and B with Purified Tubulin and in Cells Resistant to Paclitaxel (Taxol®)" *J. Biol. Chem.*, vol. 272, No. 4, 2534-2541 (1997).

Kupchan, S. M., et al., "Reductive Elimination of Epoxides to Olefins with Zinc-Copper Couple", *J. Org. Chem.*, vol. 36, No. 9, 1187-1190 (1971).

Martin, M. G., et al., "Epoxides as Alkene Protecting Groups. A Mild and Efficient Deoxygenation", *Tetrahedron Letters*, vol. 25, No. 3, 251-254 (1984).

McMurry, J. E., et al., "Reduction of Epoxides to Olefins with Low Valent Titanium", *J. Org. Chem.*, vol. 40, No. 17, 2555-2556 (1975).

McMurry, J. E., et al., "Some Deoxygenation Reactions wtih Low-Valent Titanium (TiCl$_3$/LiAlH$_4$)", *J. Org. Chem.*, vol. 43, No. 17, 3249-3254 (1978).

Meng, D., et al., "Remote Effects in Macrolide Formation Through Ring-Forming Olefin Metathesis: An Application to the Synthesis of Fully Active Epothilone Congeners", *J. Am. Chem. Soc.*, vol. 119, No. 11, 2733-2734 (1997).

Nicolaou, K. C., et al., "An Approach to Epothilones Based on Olefin Metathesis", *Angew. Chem. Int. Ed. Engl.*, vol. 35, No. 20, 2399-2401 (1996).

Nicolaou, K. C., et al., "Total Synthesis of Epothilone A: The Macrolactonization Approach", *Angew. Chem. Int. Ed. Engl.*, vol. 36, No. 5, 525-527 (1997).

Nicolaou, K. C., et al., "Designed Epothilones: Combinatorial Synthesis, Tubulin Assembly Properties, and Cytotoxic Action against Taxol-Resistant Tumor Cells", *Angew. Chem. Int. Ed. Engl.*, vol. 36, No. 19, 2097-2103 (1997).

Nicolaou, K.C., et al.; "The Olefin Metathesis Approach to Epothilone A and Its Analogues", *J. Am. Chem. Soc.*, vol. 199, No. 34, 7960-7973 (1997).

Nicolaou, K. C., et al., "Total Syntheses of Epothilones A and B via a Macrolactonization-Based Strategy", *J. Am. Chem. Soc.*, vol. 119, No. 34, 7974-7991 (1997).

Nicolaou, K. C., et al., "Synthesis of Epothilones A and B in Solid and Solution Phase", *Nature*, vol. 387, 268-272 (1997).

Nicolaou, K. C., et al., "Synthesis of Epothilones A and B in Solid and Solution Phase" (Correction to *Nature* 387, 268-272 (1997)), *Nature*, 390, 100 (1997).

Raucher, S., et al., "Total Synthesis of (+)-Dihydrocostunolide via Tandem Cope-Claisen Rearrangement", *J. Org. Chem.*, vol. 51, No. 26, 5503-5505 (1986).

Sato, M, et al., "Reduction of Organic Compounds with Low-Valent Niobium (NbCl$_5$/NaAlH$_4$)", *Chem. Letters*, 157-160 (1982).

Schinzer, D., et al., "Total Synthesis of (-)-Epothilone A", *Angew. Chem. Int. Ed. Engl.*, vol. 36, No. 5, 523-524 (1997).

Schobert, R., et al., "Reduction and Isomerization of Oxiranes and α-Diazoketones by Various Early Transition Metallocenes", *Synlett*, vol. 8, 465-466 (1990).

Sharpless, K. B., et al., "Lower Valent Tungsten Halides. A New Class of Reagents for Deoxygenation of Organic Molecules", *J. Amer. Chem. Soc.*, vol. 94, No. 18, 6538-6540 (1972).

Su, D.-S., et al., "Total Synthesis of (-)-Epothilone B: An Extension of the Suzuki Coupling Method and Insights into Structure-Activity Relationships of the Epothilones", *Angew. Chem. Int. Ed. Engl.*, vol. 36, No. 7, 757-759 (1997).

Su, D.-S., et al., "Structure-Activity Relationships of the Epothilones and the First In Vivo Comparison with Paclitaxel", *Angew. Chem. Int. Ed. Engl.*, vol. 36, No. 19, 2093-2096 (1997).

Victory, S. F., et al., "Relative Sterochemistry and Solution Conformation of the Novel Paclitaxel-Like Antimitotic Agent Epothilone A", *Bioorg. Med. Chem. Letts.*, vol. 6., No. 7, 893-898 (1996).

Winkler, J. D., et al., "A Model For The Taxol (Paclitaxel)/ Epothilone Pharmacophore", *Bioorg. Med. Chem. Letts.*, vol. 6, No. 24, 2963-2966 (1996).

Yang, Z., et al., "Total Synthesis of Epothilone A: The Olefin Metathesis Approach", *Angew. Chem. Int. Ed. Engl.*, vol. 36, No. ½, 166-168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule-Stabilising Agents", *Expert Opin. Invest. Drugs*, vol. 6, No. 7, 867-873 (1997).

Bertinato, P., et al., "Studies Toward a Synthesis of Epothilone A: Stereocontrolled Assembly of the Acyl Region and Models for Macrocyclization", J. Org. Chem., vol. 61, No. 23, 8000-8001 (1996).

*Chemical & Engineering News*, "Epothilone Epiphany: Total Syntheses", vol. 74, No. 52, 24-26 (1996).

*Chemical & Engineering News*, "First Total Synthesis of Epothilone B", vol. 75, No. 13, 23 (1997).

*Chemical & Engineering News*, "Solid-Phase Epothilone Synthesis Used to Create Analog Library", vol. 75, No. 20, 33 (1997).

Claus, E., et al., "Synthesis of the C1-C9 Segment of Epothilons", *Tetrahedron Lett.*, vol. 38, No. 8, 1359-1362 (1997).

De Brabander, J., et al., "Towards a Synthesis of Epothilone A: Rapid Assembly of the C1-C6 and C7-C12 Fragments", *Synlett*, vol. 7, 824-826 (1997).

Gabriel, T. and Wessjohann, L., "The Chromium-Reformatsky Reaction: Asymmetric Synthesis of the Aldol Fragment of the Cytotoxic Epothilons from 3-(2-Bromoacyl)-2-Oxazolidinones", *Tetrahedron Lett.*, vol. 38, No. 8, 1363-1366 (1997).

Gerth, K., et al., "Epothilons A and B: Antifungal and Cytotoxic Compounds from *Sorangiusm cellulosum* (Myxobacteria) Production, Physico-chemical and Biological Properties", *J. Antibiotics*, vol. 49, No. 6, 560-563 (1996).

Marshall, A., "Total Synthesis of Epothilone", *Nature Biotechnology*, vol. 15, No. 3, 205 (1997).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998-7999 (1996).

Meng, D., et al., "Total Syntheses of Epothilones A and B", *J. Am. Chem. Soc.*, vol. 119, No. 42, 10073-10092 (1997).

Mensching, S. and Kalesse, M., "Generation of Thiazoles by Column Dehydrogenation of Thiazolidines with MnO$_2$", *J. Prakt. Chem.*, vol. 339, No. 1, 96-97 (1997).

Mulzer, J. and Mantoulidis, A., "Synthesis of the C(1)-C(9) Segment of the Cytotoxic Macrolides Epothilon A and B", *Tetrahedron Lett.*, vol. 37, No. 51, 9179-9182 (1996).

Nicolaou, K., et al., "Chemistry, Biology and Medicine of Selected Tubulin Polymerizing Agents", *Pure Appl. Chem.*, vol. 71, No. 6, 989-997 (1999).

Nicolaou, K., et al., "Total Synthesis of Epothilone E and Related Side-chain Modified Analogues Via a Stille Coupling Based Strategy", *Bioorg. Med. Chem.*, vol. 7, No. 5, 665-697 (1999).

Schinzer, D., et al., "Studies Towards the Total Synthesis of Epothilones: Asymmetric Synthesis of the Key Fragments", *Chem. Eur. J.*, vol. 2, No. 22, 1477-1482 (1996).

Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061-2064 (1997).

Schinzer, D., et al., "Syntheses of (–)-Epothilone A", *Chem. Eur. J.*, vol. 5, No. 9, 2483-2491 (1999).

Schinzer, D., et al., "Syntheses of (–)-Epothilone B", *Chem. Eur. J.*, vol. 5, No. 9, 2492-2500 (1999).

Nicolaou, K. C., et al., "Synthesis and Biological Properties of C12, 13-Cyclopropylepothilone A and Related Epothilones", *Chemistry & Biology*, vol. 5, No. 7, 365-372 (1998).

Altmann, K.H., et al., "Epothilones and Related Structures—A New Class of Microtubule Inhibitors With Patent In Vivo Antitumor Activity," Biochim. Biophys Acta, 1470 (2000).

Nicolaou et al., "Total Synthesis of Epothilone E and Analogs with Modified Side Chains Through The Stille Coupling Reaction", Angew. Chem. Int. Ed. 37, 84-87 (1998).

Nicolaou et al., "Total Synthesis of Oxazole- and Cyclopropane-Containing Epothilone B Analogues by the Macrolactonization Approach", Chemistry, European Journal, vol. 3, No. 12, 1971-1986 (1997).

Nicolaou et al., "Chemical Biology of Epothilones", Angew. Chem. Int. Ed., 37, 2014-2045 (1988).

Hardt et al., "New Natural Epothilones from Sorangium cellulosum , Strains So ce90/B2 and So ce90/D13: Isolation, Structure Elucidation and SAR Studies", Journal of Natural Products, vol. 64, No. 7, pp. 847-856 (2001) and Electronic Supporting Information pp. 1-16.

\* cited by examiner

METHODS FOR THE PREPARATION, ISOLATION AND PURIFICATION OF EPOTHILONE B, AND X-RAY CRYSTAL STRUCTURES OF EPOTHILONE B

RELATED APPLICATIONS

This application is a divisional application of U.S. Nonprovisional patent application Ser. No. 10/668,032 filed Sep. 22, 2003, incorporated herein by reference in its entirety, which claims the benefit of U.S. Provisional Application Ser. No. 60/412,994 filed Sep. 23, 2002.

FIELD OF INVENTION

The present invention relates to improved methods for the production, isolation and purification of epothilone B. These methods include, for example, a fermentation process for the production of epothilone B, isolation via adsorption onto a resin, and subsequent purification.

BACKGROUND OF INVENTION

Epothilones are a relatively new class of macrolide compounds that were originally obtained by fermentation of myxobacteria (*Sorangium cellulosum*). These compounds were initially investigated as plant protective agents due to their anti-fungal properties. Epothilones then became of interest due to their cytotoxic activity on animal cells, and were subsequently characterized as tubulin polymerization agents. It is now known that epothilones exert microtubule-stabilizing effects similar to paclitaxel (TAXOL®) and cytotoxic activity against rapidly proliferating cells such as tumor cells or other hyperproliferative cellular disease. The use of epothilones as chemotherapeutic agents is described in Bollag et al., Cancer Research 55, 2325, 1995.

Epothilones A and B (epo A or epo B, respectively) have the structures,

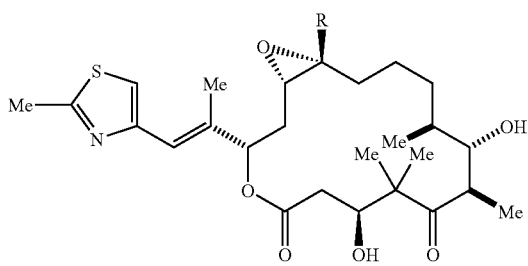

Epothilone A R=H
Epothilone B R=Me

One scheme for obtaining epothilones was revealed by Höfle et al. in WO 93/10121. Höfle cultured a strain of *Sorangium cellulosum* in a medium containing carbon sources, nitrogen sources and mineral salts. An adsorber resin was added during the culturing of the strain. The epothilones were eluted with solvent from the adsorbent resin. The various epothilones were separated by reverse-phase chromatography and crystallized. However, Höfle et al. conceded that this method produced only a low quantity of epothilone B, and also that the ratio of epothilone B to epothilone A in the fermentation was low. This low ratio of epothilone B relative to epothilone A makes recovery of pure epothilone B difficult. Thus, there is a need in the art for improved methods of fermentation to produce epothilone B in preference to epothilone A, and improved methods of isolation and purification of epothilone B.

SUMMARY OF INVENTION

The present invention is directed to an improved fermentation process for the production of epothilone B.

Further included in the present invention are new strains of *Sorangium cellulosum* obtained by mutagenesis for the production of epothilones.

Also included in the present invention are methods to improve the ratio of epothilone B to A produced by the new strain of *Sorangium cellulosum* by providing an additive to the fermentation. In one preferred embodiment, the additive is propionate, propionic acid with proper pH adjustment, or another propionate precursor.

Also included in the present invention is an improved extraction process for isolation of epothilone B from the fermentation medium using a resin. Further included are methods for washing epothilone-rich resin to reduce impurity levels and improve downstream processing.

Also included in the present invention is an improved process for the purification of epothilone B. In one embodiment, purification is achieved using crystallization. In another embodiment, purification is achieved by chromatographic methods which include normal-phase chromatography or reverse-phase chromatography. In yet another embodiment, purification is achieved by a combination of crystallization and purification of samples by chromatography, including normal and reverse-phase chromatography. In a further embodiment, the resin extract is processed by crystallization only.

Epothilone B ("epo B") is useful as an intermediate in the preparation of derivative 1 ("D1"), (as described in U.S. Pat. No. 6,262,094, herein incorporated by reference), where the 2-methyl on the thiazole ring is substituted with an amine:

Derivative 1

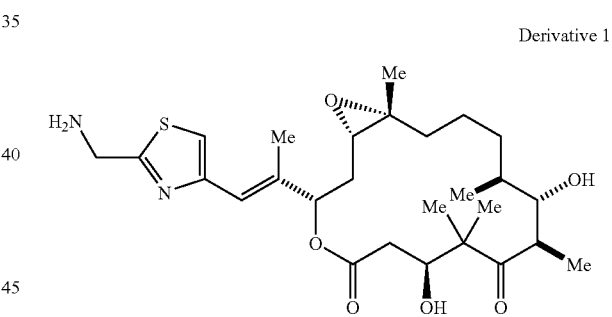

Epothilone B is also useful in the preparation of derivative 2 ("D2") (such conversion of the lactone of epothilone B to the lactam of derivative 2 is described by Borzilleri et al., J. Amer. Chem. Soc. 122, 8890, 2000, and in WO 99/02514, herein incorporated by reference):

Derivative2

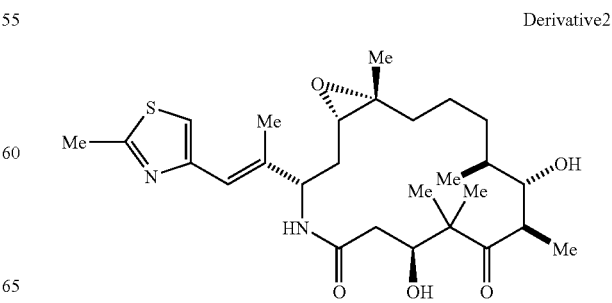

Furthermore, epothilone B ("epo B") is useful for the preparation of derivative 3 (epothilone D, "D3") (as described in U.S. Pat. No. 6,320,045, herein incorporated by reference):

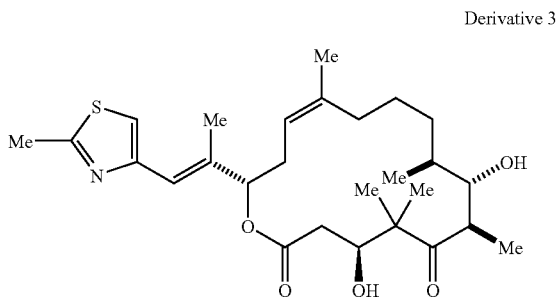

Derivative 3

Further included in the invention are crystal forms of epothilone B produced using the methods and materials described herein.

It is to be understood that both the foregoing general description and the following detailed description are exemplary, but not restrictive, of the invention.

BRIEF DESCRIPTION OF THE DRAWINGS

The advantages, nature and various features of the invention may appear more fully upon consideration of the accompanying drawings. In the drawings:

In FIG. 5, the simulated pattern was calculated from the refined atomic parameters in the monoclinic crystal structure at −33° C., and the observed pattern was measured at +23° C.

In FIG. 6, the simulated pattern was calculated from the refined atomic parameters in the monoclinic crystal structure at −33° C., and the observed pattern was measured at +23° C.

In FIG. 7, the simulated pattern was calculated from the refined atomic parameters in the monoclinic crystal structure at −40° C., and the observed pattern was measured at +23° C.

In FIG. 8, the simulated pattern was calculated from the refined atomic parameters in the monoclinic crystal structure at −3° C., and the observed pattern was measured at +23° C.

It is to be understood that these drawings are for purposes of illustrating the concepts of the invention and are not limiting in nature. In each of FIGS. 1 through 4, all methyl and methylene hydrogen atoms of the epothilone have been omitted for clarity. In FIGS. 1–4, intermolecular hydrogen bonds are shown at the bottom right and top left portions of the diagrams as dashed rods, and H-bond distances (Angstroms) designate the intermolecular oxygen—oxygen distances.

DETAILED DESCRIPTION OF THE INVENTION

Figure 1:
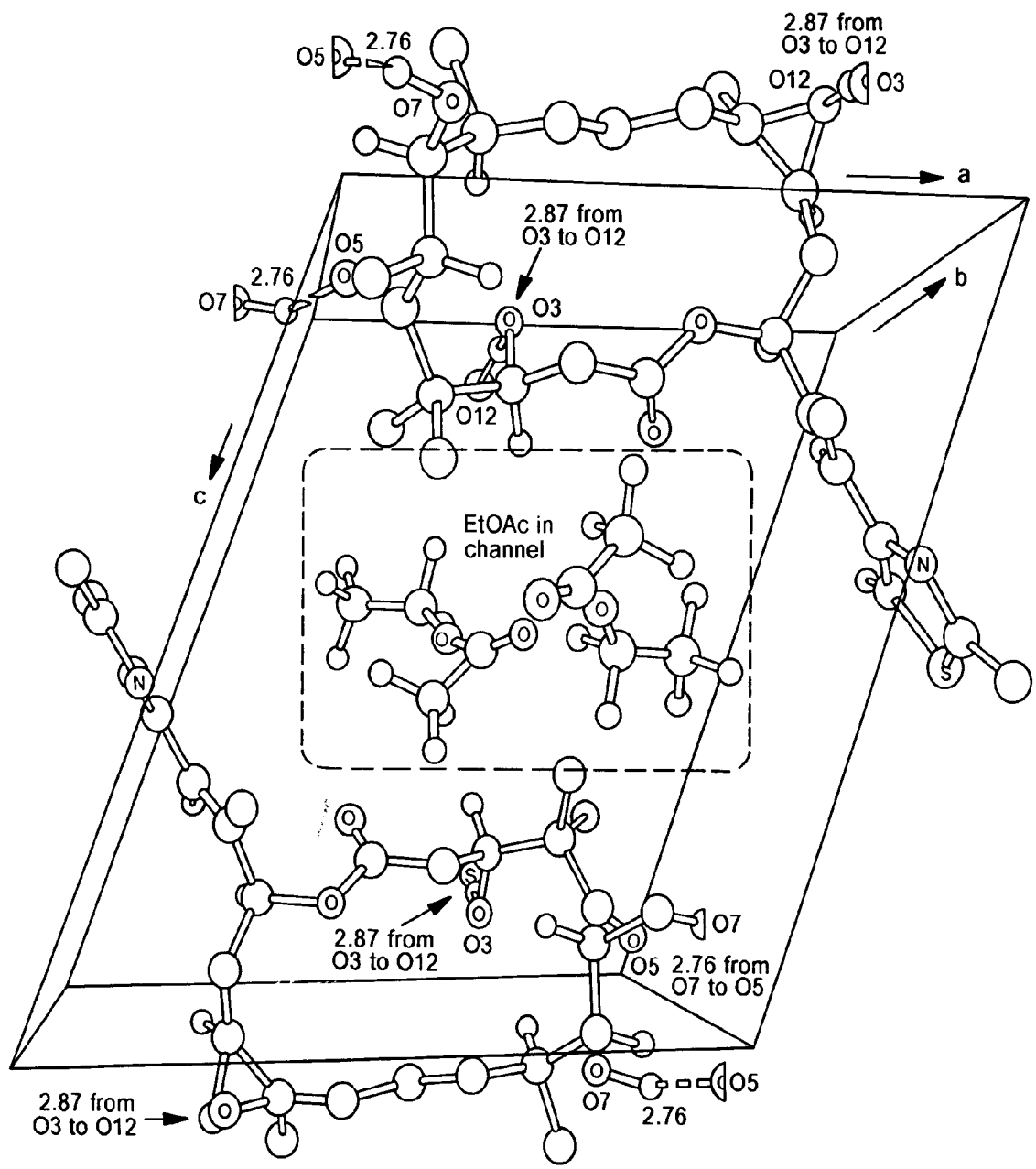
FIG. 1 shows the molecular structure in the monoclinic unit cell of form epoB-EAβ, with two molecules of epothilone B and two molecules of ethyl acetate in the guest channel of the monoclinic unit cell.

The present invention describes specific process methods and novel mutant strains of *Sorangium cellulosum*, which together or separately produce fermentations with improved concentrations of epothilone B, primarily by reduction of the relative amount of epothilone A produced during the fermentation. Cells of *Sorangium cellulosum* or other appropriate microorganisms are, for example, expanded through one or more initial growth stage cultivations, and used to provide inoculum for epothilone-producing fermentations. During the first hours of fermentation, for example in the neighborhood of 24–72 hours, cell growth occurs as the cells utilize nutrients in the medium. Thereafter, nutrients, such as vitamins, minerals, carbohydrates and amino acids (or other carbon or nitrogen sources such as amino acid precursors), are added to the medium in an amount conducive to production of epothilones. In one embodiment, the nutrients, such as vitamins, minerals, carbohydrates and amino acids are added in an amount which maintains the maximum production rate of epothilone A or epothilone B during the fermentation. In one embodiment, the maximum production rate of epothilone A or epothilone B is a production rate in which a greater amount of epothilone A or epothilone B is produced as compared to that produced without the addition of additives or nutrients or also results in a greater production rate that would occur if the additives or nutrients were added in an amount that is less than optimal. During the fermentation, propionic acid, a precursor thereof, or a salt thereof, is added in an amount effective to increase the epothilone B to epothilone A ratio (the "product ratio").

The present invention is also directed to new strains of *Sorangium cellulosum* which are useful in the manufacture of the epothilones. These new strains, particularly strain SC16408, have been obtained by mutagenesis followed by random selection.

*Sorangium cellulosum* was first isolated from a soil sample collected from the banks of the Zambesi River in South Africa in 1985. The organism was first described for production of the epothilones by Höfle et al. (cited above). The strain used by Höfle, et al. was designated So ce90, and is deposited at the Deutsche Sammiung von Mikroorganismen (German Collection of Microorganisms, DSM) under Deposit No. 6773. Strain So ce90 was subjected to UV mutagenesis followed by random selection to generate strain So ce90B2. Strain So ce90B2 (also designated SC16224) yielded epothilone B titers in shake flasks (containing for example 1.8 w/v % resin per flask) of approximately 50 mg/L or 2.8 mg/g resin (which can for example range to 3.5 or 4.5 mg/g), and a ratio of epothilone B/A of approximately 0.6.

In the present invention, strain So ce90B2 or a derivative thereof was subjected to mutagenesis with nitrosoguanidine (NTG), followed by random selection to produce strains SC16408 (which is deposited as ATCC No. PTA-3880) and SC16449 (which is deposited as ATCC No. PTA-3881). These latter two strains have been deposited with the American Type Culture Collection as patent deposits pursuant to the Budapest Treaty. Details of the selection process are set forth in the examples.

The present invention provides, in one embodiment, *Sorangium cellulosum* strains that produce (e.g., under production conditions defined below) at least about 100 mg of epothilone B per liter of broth volume. In another embodiment, the invention provides strains that produce, under epothilone B comparative production conditions, at least 80 mg of epothilone B per liter of broth volume and an epothilone B to epothilone A ratio of at least 1. The present invention provides in one embodiment strains that produce 5 mg of epothilone B/g of resin of epothilone B, or 5 mg/g resin at an epothilone B/A ratio of at least 1.0. In another embodiment, the epothilone B/A ratio is at least 1.5. In yet another embodiment, the epothilone B/A ratio is 1.5 to 4.0.

The present invention is also directed to methods to improve the ratio of epothilone B to A produced by *Sorangium cellulosum* by feeding an additive to the fermentation. In preferred embodiments, the additive comprises propionate, added after cells have grown for up to 96 hours, but preferably at approximately 24–48 hours. In some preferred embodiments, the cells were grown for approximately 34 hours before propionate was added. Early studies by GBF investigated, among other factors influencing fermentation, the effect of a one-time propionate addition to the medium at a level of 0.1% for incremental improvement in the epothilone B/epothilone A (B/A) ratio. Inventors herein have found, surprisingly, and it is one of the features of the present invention, that the titers of the epothilones, epothilone B in particular, and the B/A ratio produced in shake flasks, 14 L fermentors and production fermentors, were improved markedly by the feeding of propionate or sodium propionate. Feeding of propionate or sodium propionate produces significant improvement of epothilone B titers. For example, flask production of epothilone B was improved by supplementation with sodium propionate to within a preferred range, as monitored in the culture, of 0.05 to 0.80 mg/mL (0.005–0.08%) periodically (e.g., per day) once feeding was initiated, more preferably within a range of 0.005–0.04%. In one embodiment, the amount of propionate in the culture is targeted to 0.02% or less. In addition, other propionate-related compounds including, but not limited to propionic acid methyl ester and propionic acid ethyl ester, were also found to improve epothilone B production and subsequently the B/A ratio.

In one embodiment, particularly useful for fermentations in a flask, an additional feed containing a mixture of monobasic and dibasic phosphate is added, with the ratio selected to support an appropriate pH. This feed can be incorporated into a propionate feed or added separately.

In the present invention, a method of large scale epothilone purification is described which successfully utilizes resin addition. The inclusion of resin was found to be useful in the isolation and purification of epothilones, and also to dramatically improve the epothilone titers. In one preferred embodiment of the present invention, the resin is a styrene/divinylbenzene polymeric resin, such as an XAD resin, preferably XAD-16 or the equivalent (available as Amberlite XAD-16 from Sigma-Aldrich, St. Louis, Mo. or Rohm and Haas Co., Philadelphia, Pa.). Other Amberlite resins with hydrophobic surfaces, such as styrene-based XAD4, XAD-1180 or XAD-1600 (Rohm and Haas Co.) can also be useful in the invention, as well as resins such as styrene-based XD-207, HP20, HP21, SP825, SP850, SP700 or SP207 (which is more hydrophobic due to added bromine groups) (these resins are from Mitsubishi, Tokyo, Japan or Mitsubishi Chemical America, Inc., White Plains, N.Y.). The resin can be incorporated into the medium within a broad range, such as 0.2 w/v % to 5.0 w/v %, and preferably 1.5 w/v % to 4.0 w/v %.

The resin containing epothilones from the fermentation is optionally washed with water and either 20–30% aqueous acetonitrile or aqueous methanol to remove polar impurities, or with a solution containing detergent, preferably an ionic detergent such as an alkyl sulfate-based detergent, and an amount of an amine (added to the solution in base form). Amounts are selected to improve the quality of the epothilone extract obtained later from the resin. One preferred aqueous wash uses 0.5 w/v % sodium dodecyl sulfate and 0.5 w/v % ammonia. In this last embodiment, prior to solvent extraction the resin is preferably washed one or more times with water.

The resin containing epothilones from the fermentation is preferably extracted with a solvent that is immiscible with (phase-separates from) a water phase, such as ethyl acetate or methyl-t-butyl ether (MTBE), to remove epothilones adsorbed on the resin. Additional solvents that may be useful for extracting epothilone B include n-butanol, isopropyl acetate, n-propyl acetate, n-butyl acetate and t-butyl acetate. The rich solvent extract is preferably concentrated, and epothilone B is crystallized from the concentrate. In one embodiment, the rich solvent is washed with water, and the water-washed rich solvent is concentrated and optionally polish filtered. When the solvent is suitable, as is ethyl acetate, epothilone B is crystallized by performing a distillative solvent swap into an anti-solvent. In other words, a relatively high-boiling-point second solvent in which epothilone B is essentially insoluble is added to the rich solvent, and the rich solvent is distilled away to a sufficient degree to allow crystallization. Vacuum can be used to drive or facilitate the distillation. In one embodiment, the solvent is concentrated and a suitable amount of anti-solvent is added. Useful anti-solvents include toluene, hexanes and heptanes. The resulting slurry can be heated, and cooled to a set temperature selected to enhance the quality of the resulting crystals. Temperature oscillations can be used to improve crystal purity, minimize fines, and produce a faster-filtering slurry. For some other solvents, such as MTBE, distillative concentration of the rich solvent produces an effective crystallization environment on cooling (without the use of an anti-solvent). The resulting crystals are preferably filtered to yield a primary grade epothilone B.

During the extraction and initial crystallization epothilone B is separated from most impurities present in the initial extract, especially epothilone A. Primary grade epothilone B typically contains epothilone A as a major impurity. Also typically present are two other structurally similar impurities derived from the fermentation, namely the following oxazole analogue and the ethyl thiazole analogue:

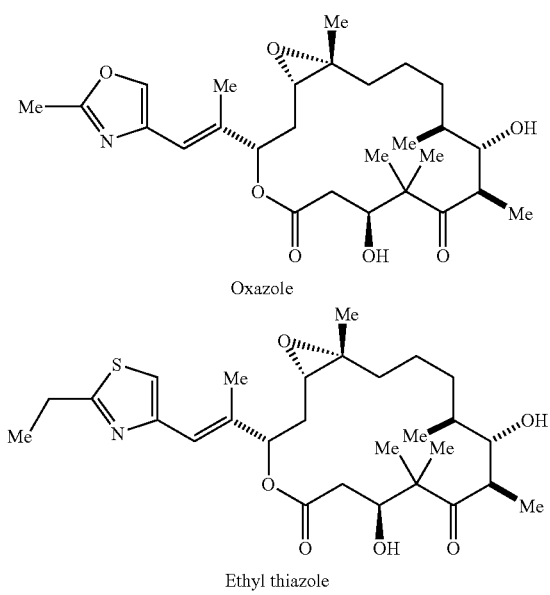

Subsequently applied purification methods (including recrystallization and chromatography steps) described herein for epothilone B involve, among other things, the removal of these two compounds to a level where they are no longer considered significant.

Primary grade epothilone B (i.e., toluene-containing crystal form epo B, primary grade), preferably obtained as described above, can then be recrystallized by heating in ethyl acetate followed by the addition of toluene with continued heating. The mixture is then cooled, the resulting crystalline slurry is filtered and the cake washed with toluene to give once recrystallized epothilone B (i.e., toluene-containing crystal form epo B, recrystallized) Alternatively, primary grade epothilone B can be processed through a preparative high performance reverse-phase chromatography step (e.g., on RP/C-18 in the form of a column) as set forth in the examples. Optionally, prior to loading the epothilone sample onto the column, a preceding volume of a suitable organic solvent, or a mixture of organic solvents, is added to reduce precipitation of the epothilone. In one embodiment, the organic solvent is one such as dimethylsulfoxide (DMSO). Optionally, a trailing volume of a suitable organic solvent or a mixture of organic solvents is added to reduce precipitation of the epothilone. Epothilones are then eluted with a suitable organic solvent, a mixture of organic solvents or an aqueous solution of an organic solvent. In one embodiment, the epothilones are eluted with a mixture of acetonitrile and water. The elution profile using these solvents can, for example, be linear or gradient, and is chosen to obtain low impurity levels. Fractions containing epothilone B of desired purity are pooled, concentrated, and extracted with a solvent including, but not limited to, ethyl acetate. The rich solvent extracts are then concentrated and crystallized, for example, by the addition of a low-polarity solvent such as n-heptane or heptanes, and optionally cooled. The slurry is filtered, washed with solvent/anti-solvent (in a ratio and amount selected to not dissolve significant amounts of epothilone B), such as ethyl acetate/n-heptane in a 2:1 ratio. The washed crystals are dried to yield high-quality epothilone B.

Other purification methods can be used, such as chromatography on normal phases such as silica, or silica based normal phases and the like. For example, high performance normal phase chromatography can be used. Samples can be loaded onto the column in a relatively low-polarity solvent such as methylene chloride, and the epothilones eluted with higher-polarity solvent, such as a mixture of ethyl acetate and heptane. The elution profile using these solvents can, for example, be linear or gradient, and is chosen to obtain low impurity levels. The desired fractions are pooled, concentrated and crystallized, for example from ethyl acetate by the addition of a low-polarity solvent such as n-heptane, heptanes, or toluene. The slurry is filtered, washed with solvent/anti-solvent (in a ratio and amount selected to not dissolve significant amounts of epothilone B), such as ethyl acetate/n-heptane in a 2:1 ratio or ethyl acetate/toluene. The washed crystals are dried to yield high quality epothilone B.

In certain cases where extensive removal of the ethyl thiazole or oxazole analogs is not required, such as in the synthesis of D1, epothilone B can be purified by crystallization alone. Solid epothilone B material is dissolved, for example, in warm ethyl acetate and crystallized (or recrystallized) by cooling to ambient temperature or cooler, followed by filtration and drying (e.g., in vacuo). Crystallizations can be repeated to obtain the desired purity, such as 2 to 3 times.

Growth medium for growing the epothilone-producing microorganism can be, for example, formulated as follows:

| Ingredient | Preferred (g/L) | More Preferred (g/L) | Still More Preferred (g/L) |
| --- | --- | --- | --- |
| Powdered Skim Milk | 0.5–12 | 1–8 | 2–6 |
| Toasted Nutrisoy Flour[1] | 0.5–12 | 1–8 | 2–6 |
| Tastone - 154[1] | 0.5–12 | 1–6 | 1–4 |
| Maltrin-M040[1] | 4–18 | 6–14 | 8–12 |
| $CaCl_2.2H_2O$ | 0.2–2.4 | 0.4–1.6 | 0.8–1.2 |
| $MgSO_4.7H_2O$ | 0.2–2.4 | 0.4–1.6 | 0.8–1.2 |
| EDTA, FeIII, Na salt | 0.002–0.02 | 0.004–0.016 | 0.006–0.014 |
| HEPES | 6–20 | 8–16 | 10–14 |
| Glycerol | 0.5–12 | 1–8 | 2–6 |

[1]Other skim milk, soy flours, yeast extracts and Maltrin starches have also been used interchangeably with comparable results.

Production medium for growing the epothilone-producing microorganism and for production of epothilones, especially in shake flasks, can be for example formulated as above with the following difference with respect to glycerol, and the following addition of resin:

| Ingredient | Preferred (g/L) | More Preferred (g/L) | Still More Preferred (g/L) |
| --- | --- | --- | --- |
| Glycerol | 2–20 | 4–16 | 6–14 |
| Resin | 10–40 | 12–35 | 15–30 |

A useful nutrient feed solution, especially for use in shake flasks, comprises:

| Ingredient | Preferred (%) |
| --- | --- |
| Sodium Propionate | 2–5 |
| Maltrin-M040 | 8–12 |
| Tastone-154 | 2–5 |

Such nutrient feed can further contain a mixture of dibasic sodium phosphate and monosodium phosphate, as follows:

| Ingredient | Preferred (%) |
| --- | --- |
| Disodium phosphate | 1.0–2.0 |
| Monosodium phosphate | 0.3–0.7 |

The ratio of disodium phosphate to monosodium phosphate is selected to minimize pH drift of the culture away from the desired pH upon addition of feed.

For use in fermentors, the nutrient components described above, with the exception of HEPES, which is preferably deleted, can preferably be used with antifoam (e.g., from Dow Corning, AF Emulsion, Food Grade) added as follows:

| Ingredient | Preferred (g/L) | More Preferred (g/L) | Still More Preferred (g/L) |
| --- | --- | --- | --- |
| Antifoam | 0.5–5 | 1–4.5 | 1.5–4 |

Caustic (sodium or potassium hydroxide solution) can be added to the fermentation medium as needed to maintain a useful pH range. Resin can be added as follows:

| Ingredient | Preferred (g/L) | More Preferred (g/L) | Still More Preferred (g/L) |
| --- | --- | --- | --- |
| Resin | 10–50 | 12–45 | 15–40 |

In the production fermentation, propionate and nutrients are preferably added separately as needed. Propionate feed can, for example, comprise 80 to 150 g/L sodium propionate, with the amount most preferably added to maintain (e.g., as determined by HPLC) propionate levels of 0.05 to 0.20 mg/mL. Propionate addition can be initiated 20–40 hours after adding the seed culture into the fermentor. The nutrients are supplemented, for example, with a sterile feeder stock as follows:

| Ingredient | Preferred (g/L) |
| --- | --- |
| Tastone-154 | 15–25 |
| Maltrin-M040 | 55–75 |
| Antifoam | 0.5–1.5 |

For longer term fermentations, additional nutrients are preferably added, for example, from the following sterile feeder stock, which is added in higher volume compared to the preceding feeder stock:

| Ingredient | Preferred (g/L) |
| --- | --- |
| Powdered Skim Milk | 40–60 |
| Maltrin-M040 | 140–180 |
| Glycerol | 60–90 |
| Antifoam | 0.5–1.5 |

These nutrients of the above two feeds can be selected to avoid initiating a growth phase.

The present invention includes processes for the production of epothilone B wherein the epothilone B ("epo B") is converted to Derivative 1 ("D1") as described in U.S. Pat. No. 6,262,094, herein incorporated by reference), having the following formula:

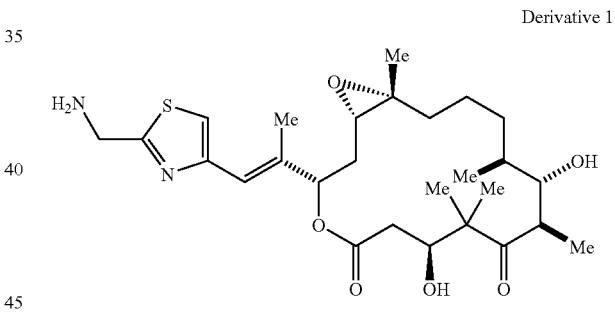

Derivative 1

The present invention also includes processes for the production of epothilone B wherein the epothilone B is converted to Derivative 2 ("D2") (described by Borzilleri et al., J. Amer. Chem. Soc. 122, 8890, 2000, and in WO 99/02514, herein incorporated by reference), having the formula:

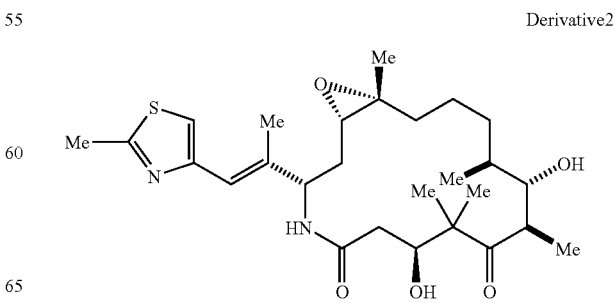

Derivative 2

The present invention further includes processes for the production of epothilone B wherein the epothilone B ("epo B") is converted to Derivative 3 (epothilone D, "D3") (as described in U.S. Pat. No. 6,320,045, herein incorporated by reference), having the following formula:

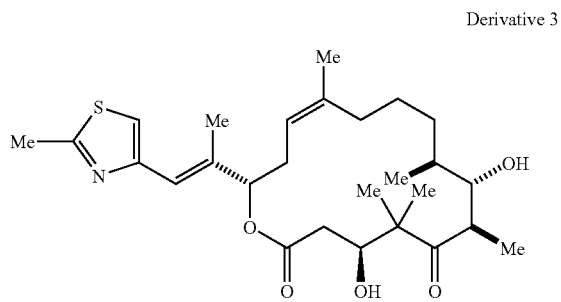

Derivative 3

Crystal Forms of Epothilone B

Applicants also have made various crystal forms of epothilone B using the inventive methods and materials described herein. Epothilone B crystals have been obtained using different solvents and solvent systems. For example, applicants have discovered a toluene-containing epothilone B solvated crystal form, designated herein as epoB-Toβ, having the unit cell data reported below in Table 1. The toluene-containing solvated crystal form of epothilone B is further illustrated with FIGS. 9 through 12 and FIGS. 15 and 16 herein. Applicants also have obtained epothilone B crystals using acetonitrile (i.e., epoB-ANβ), ethyl acetate (i.e., epoB-Eaβ), and isopropyl alcohol (i.e., epoB-Ipβ), as well as the solvent systems described below in the examples. These crystallographically isostructural forms have a monoclinic clathrate structure with a P2$_1$ space group containing lipophilic solvent channels that extend along the b-axis throughout the crystals (1 channel/unit cell). Each channel can contain up to two solvent molecules such as toluene, acetonitrile, ethyl acetate, isopropyl alcohol, or MTBE (ideally resulting in 1:1 solvates of epothilone B). Crystallization from toluene/ethyl acetate solvent mixtures (e.g., 1:1 mixture) results in preferential incorporation of toluene in the clathrate channels (i.e., obtain form epoB-TOβ, not epoB-EAβ). Both hydrogen-bond donors of the epothilone (hydroxyls) are involved in interepothilone hydrogen bonds and are not available to bind to, and constrain, the guest solvents.

Forms epoB-TOβ, epoB-ANβ, epoB-EAβ, and epoB-IPβ display the unit cell data presented in Table I. Crystallization conditions for obtaining these forms of crystals containing toluene, acetonitrile, ethyl acetate and isopropanol are presented below in the examples. PXRD patterns for the crystals prepared using the methods described in Example 7 are set forth in FIGS. 9, 11, and 13, also as further described below.

Tabulated specific exemplary parameters for these crystal forms are as follows, and as shown in Table 1:

| Form | | |
|---|---|---|
| epoB-Toβ | Crystallized from toluene as described in Example 8A. | |
| epoB-ANβ | Crystallized from acetonitrile as described in Example 8B. | |
| epoB-EAβ | Crystallized from ethyl acetate (EtOAc) as described in Example 8C. | |
| epoB-IPβ | Crystallized from isopropyl alcohol (IPA) as described in Example 8D. | |

Figure 9:
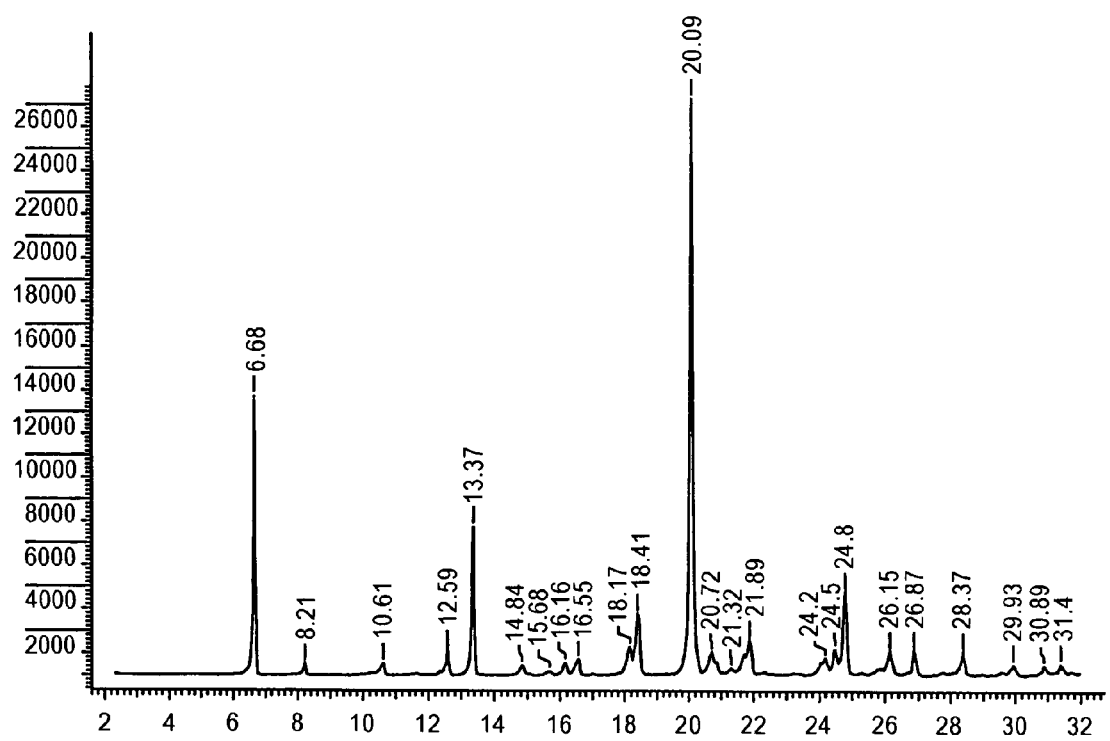
FIG. 9 shows an observed PXRD pattern for a toluene-containing primary grade solvate of epothilone B produced following the method described in Example 7, Step A.
Figure 10:
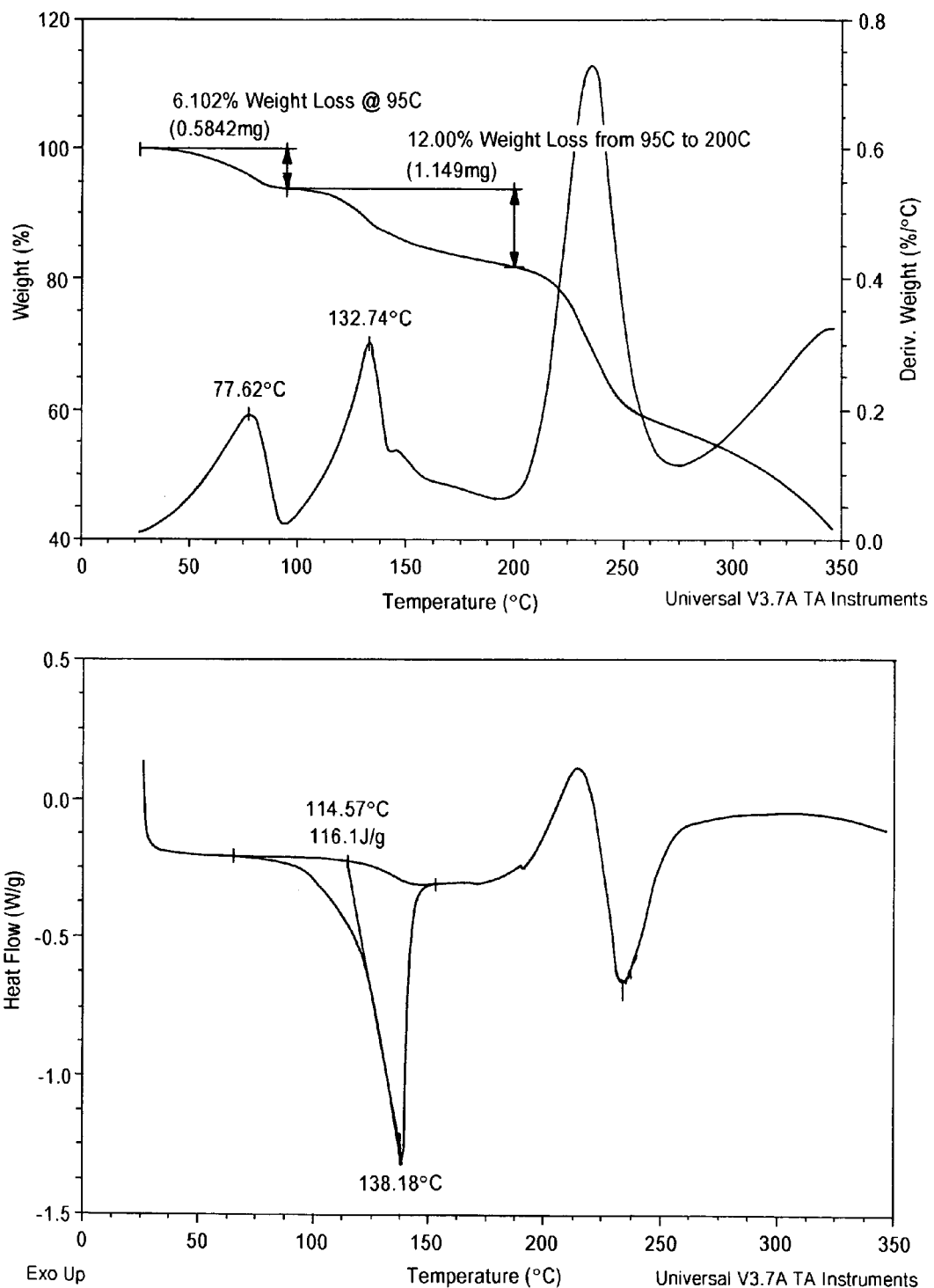
FIG. 10 shows the thermal analysis (DSC and TGA) for the toluene-containing primary grade solvate of FIG. 9.
Figure 11:
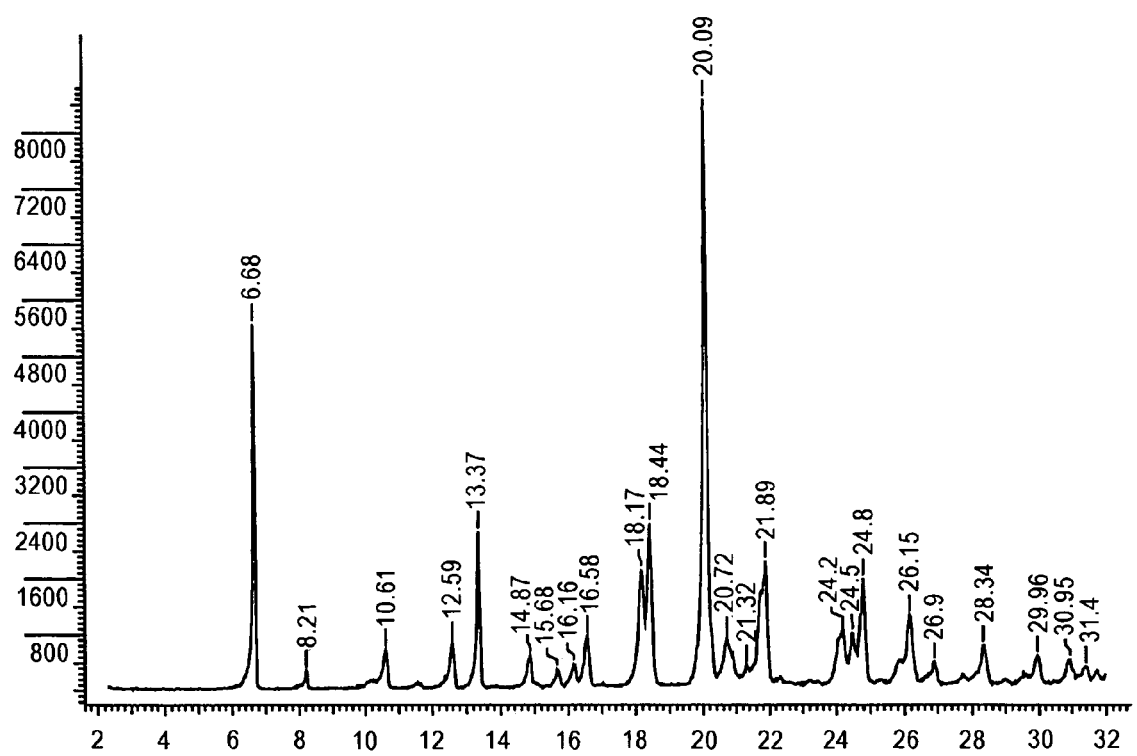
FIG. 11 shows an observed PXRD pattern for a toluene-containing recrystallized solvate of epothilone B, produced following the method described in Example 7, Step B.
Figure 13:
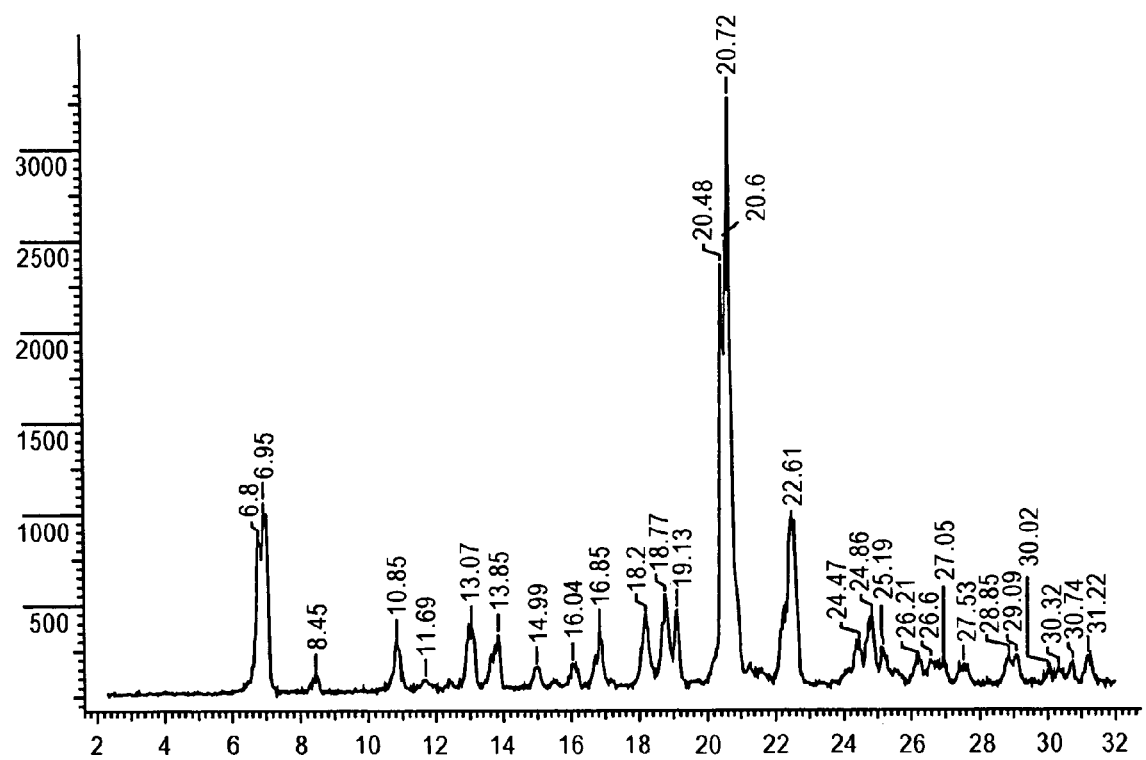
FIG. 13 shows an observed PXRD pattern for the ethyl acetate containing solvate of epothilone B, produced following the method described in Example 7, Step C.

Fractional atomic coordinates for epoB-ANβ, epoB-EAβ, epoB-IPβ and epoB-Toβ are shown in Tables 2, 3, 4 and 5, respectively. The PXRD patterns set forth in FIGS. 9, 11 and 13 are characterized by the data listed in Tables 6, 7 and 8, below.

TABLE 1

Unit cell data

| Form | T(°C.) | a(Å) | b(Å) | c(Å) | B | V | Z | V/Z | sg | d(calc)[1] | R | Ideal solvent sites |
|---|---|---|---|---|---|---|---|---|---|---|---|---|
| Epo B-TOβ | −33 | 11.853(1) | 10.613(2) | 14.328(2) | 113.04(1) | 1659(1) | 2 | 829 | P2$_1$ | 1.201 | 0.09 | 1 toluene per epo B |
| Epo B-ANβ | −40 | 11.961(1) | 10.543(1) | 13.601(2) | 111.89(1) | 1592(1) | 2 | 796 | P2$_1$ | 1.145 | 0.07 | 1 acetonitrile per epo B |
| Epo B-EAβ | −33 | 11.939(1) | 10.587(1) | 13.882(1) | 111.87(1) | 1628(1) | 2 | 814 | P2$_1$ | 1.215 | 0.07 | 1 EtOAc per epo B |
| EpoB-Ipβ | −3 | 11.928(2) | 10.610(1) | 13.870(2) | 111.92(1) | 1628(1) | 2 | 814 | P2$_1$ | 1.158 | 0.09 | 1 IPA per epo B |

[1]Ideal densities calculated. assuming 1:1 solvent occupancy.

TABLE 2

Fractional Atomic Coordinates for Epothilone B Acetonitrile Solvate, Form EpoB-ANβ (most hydrogen atoms have been omitted)

| Atom | X | Y | Z |
|---|---|---|---|
| C1 | 0.4422 | 0.2380 | 0.3076 |
| C2 | 0.5619 | 0.2882 | 0.3165 |
| C3 | 0.6422 | 0.1833 | 0.3013 |
| C4 | 0.7565 | 0.2263 | 0.2807 |
| C5 | 0.8531 | 0.2847 | 0.3800 |
| C6 | 0.8409 | 0.4180 | 0.4193 |
| C7 | 0.8968 | 0.4218 | 0.5419 |
| C8 | 0.8360 | 0.3345 | 0.5975 |
| C9 | 0.7205 | 0.3935 | 0.6018 |
| C10 | 0.6345 | 0.2947 | 0.6184 |
| C11 | 0.5287 | 0.3609 | 0.6355 |
| C12 | 0.4328 | 0.2722 | 0.6397 |
| C13 | 0.3118 | 0.2674 | 0.5573 |
| C14 | 0.2626 | 0.3435 | 0.4562 |
| C15 | 0.2748 | 0.2789 | 0.3613 |
| O16 | 0.3977 | 0.3084 | 0.3684 |
| C16 | 0.7197 | 0.3194 | 0.1878 |
| C17 | 0.8080 | 0.1051 | 0.2508 |
| C18 | 0.9083 | 0.5112 | 0.3717 |
| C19 | 0.9258 | 0.3048 | 0.7095 |
| C20 | 0.4763 | 0.1572 | 0.7109 |
| C21 | 0.1833 | 0.3270 | 0.2580 |
| C22 | 0.1927 | 0.4656 | 0.2359 |

TABLE 2-continued

Fractional Atomic Coordinates for Epothilone B Acetonitrile Solvate, Form EpoB-ANβ (most hydrogen atoms have been omitted)

| Atom | X | Y | Z | |
|---|---|---|---|---|
| C23 | 0.1008 | 0.2458 | 0.1993 | |
| C24 | −0.0043 | 0.2676 | 0.1034 | |
| C25 | −0.0708 | 0.1728 | 0.0409 | |
| C26 | −0.1519 | 0.3799 | −0.0163 | |
| C27 | −0.2252 | 0.4942 | −0.0664 | |
| S | −0.1936 | 0.2297 | −0.0595 | |
| N | −0.0507 | 0.3873 | 0.0719 | |
| O1 | 0.3897 | 0.1501 | 0.2552 | |
| O2 | 0.6748 | 0.1045 | 0.3926 | |
| O5 | 0.9464 | 0.2278 | 0.4266 | |
| O7 | 0.8893 | 0.5485 | 0.5778 | |
| O12 | 0.3313 | 0.3359 | 0.6550 | |
| H3 | 0.5936 | 0.1283 | 0.2313 | |
| H6 | 0.7466 | 0.4426 | 0.3937 | |
| H7 | 0.9913 | 0.3942 | 0.5683 | |
| H8 | 0.8117 | 0.2471 | 0.5514 | |
| H13 | 0.2618 | 0.1794 | 0.5410 | |
| H15 | 0.2633 | 0.1778 | 0.3662 | |
| H3O | 0.6691 | 0.0154 | 0.3705 | |
| H7O | 0.9636 | 0.5994 | 0.5825 | |
| N27 | 0.4609 | 0.5049 | 0.0188 | (acetonitrile) |
| C28 | 0.3963 | 0.4080 | 0.0038 | (acetonitrile) |
| C29 | 0.3379 | 0.2975 | −0.0775 | (acetonitrile) |

TABLE 3

Fractional Atomic Coordinates for Epothilone B, Ethyl Acetate Solvate, Form EpoB-EAβ (most hydrogen atoms have been omitted)

| Atom | X | Y | Z |
|---|---|---|---|
| C1 | 0.4400 | 0.2438 | 0.3107 |
| C2 | 0.5605 | 0.2943 | 0.3190 |
| C3 | 0.6416 | 0.1904 | 0.3056 |
| C4 | 0.7559 | 0.2327 | 0.2857 |
| C5 | 0.8532 | 0.2913 | 0.3822 |
| C6 | 0.8410 | 0.4228 | 0.4212 |
| C7 | 0.8957 | 0.4275 | 0.5404 |
| C8 | 0.8319 | 0.3405 | 0.5928 |
| C9 | 0.7164 | 0.4000 | 0.5966 |
| C10 | 0.6298 | 0.3042 | 0.6134 |
| C11 | 0.5231 | 0.3717 | 0.6266 |
| C12 | 0.4266 | 0.2844 | 0.6321 |
| C13 | 0.3066 | 0.2780 | 0.5503 |
| C14 | 0.2581 | 0.3526 | 0.4526 |
| C15 | 0.2706 | 0.2867 | 0.3589 |
| O16 | 0.3940 | 0.3148 | 0.3668 |
| C16 | 0.7203 | 0.3272 | 0.1940 |
| C17 | 0.8079 | 0.1121 | 0.2559 |
| C18 | 0.9092 | 0.5160 | 0.3757 |
| C19 | 0.9227 | 0.3099 | 0.7056 |
| C20 | 0.4667 | 0.1703 | 0.7040 |
| C21 | 0.1800 | 0.3335 | 0.2576 |
| C22 | 0.1887 | 0.4688 | 0.2331 |
| C23 | 0.0962 | 0.2506 | 0.2011 |
| C24 | −0.0076 | 0.2687 | 0.1042 |
| C25 | −0.0762 | 0.1706 | 0.0472 |
| C26 | −0.1515 | 0.3743 | −0.0242 |
| C27 | −0.2158 | 0.4821 | −0.0821 |
| S | −0.1923 | 0.2232 | −0.0566 |
| N | −0.0487 | 0.3847 | 0.0652 |
| O1 | 0.3878 | 0.1559 | 0.2575 |
| O3 | 0.6749 | 0.1137 | 0.3972 |
| O6 | 0.9464 | 0.2337 | 0.4280 |
| O7 | 0.8889 | 0.5526 | 0.5755 |
| O12 | 0.3257 | 0.3484 | 0.6457 |
| H3 | 0.5927 | 0.1346 | 0.2372 |
| H6 | 0.7463 | 0.4478 | 0.3947 |
| H7 | 0.9884 | 0.3992 | 0.5620 |
| H8 | 0.8080 | 0.2533 | 0.5499 |

TABLE 3-continued

Fractional Atomic Coordinates for Epothilone B, Ethyl Acetate Solvate, Form EpoB-EAβ (most hydrogen atoms have been omitted)

| Atom | X | Y | Z | |
|---|---|---|---|---|
| H13 | 0.2573 | 0.1911 | 0.5357 | |
| H15 | 0.2575 | 0.1863 | 0.3624 | |
| H3O | 0.6713 | 0.0150 | 0.3759 | |
| H7O | 0.9745 | 0.5994 | 0.5930 | |
| O28 | 0.5242 | 0.5794 | 0.0077 | (ethyl acetate) |
| O31 | 0.4179 | 0.4326 | 0.0063 | (ethyl acetate) |
| C28 | 0.4731 | 0.5098 | 0.0256 | (ethyl acetate) |
| C29 | 0.4265 | 0.4705 | 0.0892 | (ethyl acetate) |
| C31 | 0.3610 | 0.3621 | −0.0408 | (ethyl acetate) |
| C30 | 0.2548 | 0.3272 | −0.0460 | (ethyl acetate) |

TABLE 4

Fractional Atomic Coordinates for Epothilone B, Isopropyl Alcohol Solvate, Form EpoB-IPβ (most hydrogen atoms have been omitted)

| Atom | X | Y | Z | |
|---|---|---|---|---|
| C1 | 0.4418 | 0.2548 | 0.3104 | |
| C2 | 0.5609 | 0.3055 | 0.3186 | |
| C3 | 0.6429 | 0.2009 | 0.3049 | |
| C4 | 0.7565 | 0.2462 | 0.2851 | |
| C5 | 0.8541 | 0.3018 | 0.3837 | |
| C6 | 0.8410 | 0.4357 | 0.4229 | |
| C7 | 0.8977 | 0.4390 | 0.5415 | |
| C8 | 0.8345 | 0.3493 | 0.5940 | |
| C9 | 0.7184 | 0.4107 | 0.5972 | |
| C10 | 0.6325 | 0.3111 | 0.6156 | |
| C11 | 0.5261 | 0.3793 | 0.6303 | |
| C12 | 0.4292 | 0.2892 | 0.6329 | |
| C13 | 0.3087 | 0.2842 | 0.5528 | |
| C14 | 0.2607 | 0.3630 | 0.4551 | |
| C15 | 0.2736 | 0.2932 | 0.3613 | |
| O16 | 0.3950 | 0.3241 | 0.3669 | |
| C16 | 0.7179 | 0.3380 | 0.1935 | |
| C17 | 0.8084 | 0.1250 | 0.2541 | |
| C18 | 0.9098 | 0.5290 | 0.3774 | |
| C19 | 0.9269 | 0.3222 | 0.7069 | |
| C20 | 0.4742 | 0.1736 | 0.7031 | |
| C21 | 0.1807 | 0.3387 | 0.2590 | |
| C22 | 0.1879 | 0.4780 | 0.2352 | |
| C23 | 0.1028 | 0.2530 | 0.2009 | |
| C24 | −0.0041 | 0.2724 | 0.1029 | |
| C25 | −0.0678 | 0.1712 | 0.0456 | |
| C26 | −0.1517 | 0.3781 | −0.0198 | |
| C27 | −0.2289 | 0.4888 | −0.0775 | |
| S | −0.1896 | 0.2262 | −0.0575 | |
| N | −0.0526 | 0.3893 | 0.0653 | |
| O1 | 0.3903 | 0.1657 | 0.2594 | |
| O3 | 0.6763 | 0.1239 | 0.3954 | |
| O5 | 0.9485 | 0.2459 | 0.4293 | |
| O7 | 0.8898 | 0.5642 | 0.5781 | |
| O12 | 0.3283 | 0.3539 | 0.6476 | |
| H3 | 0.5946 | 0.1457 | 0.2365 | |
| H6 | 0.7464 | 0.4597 | 0.3977 | |
| H7 | 0.9915 | 0.4115 | 0.5668 | |
| H8 | 0.8111 | 0.2625 | 0.5504 | |
| H13 | 0.2582 | 0.1971 | 0.5380 | |
| H15 | 0.2640 | 0.1927 | 0.3679 | |
| H3O | 0.6731 | 0.0260 | 0.3733 | |
| H7O | 0.9599 | 0.6223 | 0.5696 | |
| O28 | 0.4344 | 0.2122 | 0.0495 | (isopropyl alcohol) |
| C28 | 0.3601 | 0.2863 | −0.0462 | (isopropyl alcohol) |
| C30 | 0.4351 | 0.3798 | −0.0762 | (isopropyl alcohol) |
| C29 | 0.2460 | 0.3279 | −0.0487 | (isopropyl alcohol) |

TABLE 5

Fractional Atomic Coordinates for Epothilone B, Toluene Solvate, Form EpoB-TOβ (most hydrogen atoms have been omitted)

| Atom | X | Y | Z | |
|---|---|---|---|---|
| C1 | 0.4314 | 0.2211 | 0.3158 | |
| C2 | 0.5581 | 0.2739 | 0.3228 | |
| C3 | 0.6395 | 0.1704 | 0.3110 | |
| C4 | 0.7506 | 0.2081 | 0.2888 | |
| C5 | 0.8509 | 0.2746 | 0.3880 | |
| C6 | 0.8414 | 0.4043 | 0.4212 | |
| C7 | 0.8976 | 0.4053 | 0.5382 | |
| C8 | 0.8372 | 0.3234 | 0.5911 | |
| C9 | 0.7204 | 0.3812 | 0.5930 | |
| C10 | 0.6312 | 0.2790 | 0.6075 | |
| C11 | 0.5255 | 0.3494 | 0.6227 | |
| C12 | 0.4302 | 0.2588 | 0.6250 | |
| C13 | 0.3014 | 0.2537 | 0.5473 | |
| C14 | 0.2538 | 0.3361 | 0.4501 | |
| C15 | 0.2643 | 0.2640 | 0.3626 | |
| O16 | 0.3877 | 0.2964 | 0.3648 | |
| C16 | 0.7158 | 0.3123 | 0.2026 | |
| C17 | 0.8082 | 0.0907 | 0.2610 | |
| C18 | 0.9061 | 0.4961 | 0.3806 | |
| C19 | 0.9323 | 0.2951 | 0.6989 | |
| C20 | 0.4703 | 0.1447 | 0.6945 | |
| C21 | 0.1702 | 0.3170 | 0.2598 | |
| C22 | 0.1709 | 0.4486 | 0.2391 | |
| C23 | 0.0898 | 0.2230 | 0.2030 | |
| C24 | −0.0145 | 0.2462 | 0.1060 | |
| C25 | −0.0811 | 0.1430 | 0.0546 | |
| C26 | −0.1432 | 0.3561 | −0.0251 | |
| C27 | −0.2089 | 0.4563 | −0.0926 | |
| S | −0.1987 | 0.1985 | −0.0555 | |
| N | −0.0507 | 0.3632 | 0.0580 | |
| O1 | 0.3838 | 0.1303 | 0.2676 | |
| O3 | 0.6742 | 0.0956 | 0.3983 | |
| O5 | 0.9468 | 0.2169 | 0.4313 | |
| O7 | 0.8912 | 0.5329 | 0.5727 | |
| O12 | 0.3254 | 0.3255 | 0.6408 | |
| H3 | 0.5816 | 0.1062 | 0.2496 | |
| H6 | 0.7457 | 0.4264 | 0.3944 | |
| H7 | 0.9919 | 0.3719 | 0.5628 | |
| H8 | 0.8141 | 0.2297 | 0.5521 | |
| H13 | 0.2871 | 0.1529 | 0.5221 | |
| H15 | 0.2567 | 0.1589 | 0.3722 | |
| H3O | 0.6633 | −0.0002 | 0.3785 | |
| H7O | 0.9663 | 0.5756 | 0.5776 | |
| C28 | 0.4258 | 0.4317 | 0.0030 | (toluene) |
| C29 | 0.3526 | 0.3996 | 0.0429 | (toluene) |
| C30 | 0.2586 | 0.3239 | 0.0126 | (toluene) |
| C31 | 0.2245 | 0.2386 | −0.0713 | (toluene) |
| C32 | 0.2984 | 0.2800 | −0.1182 | (toluene) |
| C33 | 0.3923 | 0.3496 | −0.1016 | (toluene) |
| C34 | 0.5043 | 0.4979 | −0.0119 | (toluene) |

TABLE 6

PXRD Data for Epothilone B, Toluene Containing Solvate, Produced Using the Method of Example 7, Step A and Shown in FIG. 9

| Scattering angle (deg. 2-theta) | d-spacing (A) | Relative Intensity (%) |
|---|---|---|
| 6.680 | 13.2212 | 48.5 |
| 8.210 | 10.7604 | 2.1 |
| 10.610 | 8.3312 | 2.2 |
| 12.590 | 7.0251 | 4.3 |
| 13.370 | 6.6169 | 25.8 |
| 14.840 | 5.9646 | 1.9 |
| 15.680 | 5.6469 | 0.9 |
| 16.160 | 5.4802 | 2.3 |
| 16.550 | 5.3520 | 2.9 |
| 18.170 | 4.8783 | 5.0 |
| 18.410 | 4.8152 | 10.6 |
| 20.090 | 4.4162 | 100.0 |
| 20.720 | 4.2833 | 4.2 |
| 21.320 | 4.1641 | 1.4 |
| 21.890 | 4.0570 | 6.3 |
| 24.200 | 3.6747 | 3.2 |
| 24.500 | 3.6304 | 4.7 |
| 24.800 | 3.5871 | 14.4 |
| 26.150 | 3.4049 | 4.4 |
| 26.870 | 3.3153 | 4.5 |
| 28.370 | 3.1433 | 4.3 |
| 29.930 | 2.9829 | 2.2 |
| 30.890 | 2.8924 | 2.0 |
| 31.400 | 2.8466 | 2.2 |

TABLE 7

PXRD Data for Epothilone B, Toluene Containing Solvate, Produced Using the Method of Example 7, Step B, and Shown in FIG. 11

| Scattering angle (deg. 2-theta) | d-spacing (A) | Relative Intensity (%) |
|---|---|---|
| 6.680 | 13.2212 | 62.1 |
| 8.210 | 10.7604 | 3.4 |
| 10.610 | 8.3312 | 6.9 |
| 12.590 | 7.0251 | 8.1 |
| 13.370 | 6.6169 | 26.9 |
| 14.870 | 5.9526 | 5.9 |
| 15.680 | 5.6469 | 3.7 |
| 16.160 | 5.4802 | 4.5 |
| 16.580 | 5.3424 | 9.1 |
| 18.170 | 4.8783 | 20.3 |
| 18.440 | 4.8075 | 28.2 |
| 20.090 | 4.4162 | 100.0 |
| 20.720 | 4.2833 | 9.0 |
| 21.320 | 4.1641 | 4.4 |
| 21.890 | 4.0570 | 21.8 |
| 24.200 | 3.6747 | 10.8 |
| 24.500 | 3.6304 | 9.7 |
| 24.800 | 3.5871 | 18.9 |
| 26.150 | 3.4049 | 12.8 |
| 26.900 | 3.3117 | 4.9 |
| 28.340 | 3.1466 | 7.6 |
| 29.960 | 2.9800 | 5.9 |
| 30.950 | 2.8869 | 5.3 |
| 31.400 | 2.8466 | 4.1 |

TABLE 8

PXRD Data for Epothilone B, Ethyl Acetate Containing Solvate, Produced Using the Method of Example 7, Step C, and Shown in FIG. 13

| Scattering angle (deg. 2-theta) | d-spacing (A) | Relative Intensity (%) |
|---|---|---|
| 6.800 | 12.9881 | 26.2 |
| 6.950 | 12.7082 | 32.5 |
| 8.450 | 10.4553 | 4.0 |
| 10.850 | 8.1474 | 9.4 |
| 11.690 | 7.5638 | 2.8 |
| 13.070 | 6.7681 | 11.6 |
| 13.850 | 6.3887 | 10.2 |
| 14.990 | 5.9053 | 4.7 |
| 16.040 | 5.5210 | 5.4 |
| 16.850 | 5.2574 | 11.0 |

TABLE 8-continued

PXRD Data for Epothilone B, Ethyl Acetate Containing Solvate, Produced Using the Method of Example 7, Step C, and Shown in FIG. 13

| Scattering angle (deg. 2-theta) | d-spacing (A) | Relative Intensity (%) |
|---|---|---|
| 18.200 | 4.8703 | 13.5 |
| 18.770 | 4.7237 | 16.9 |
| 19.130 | 4.6356 | 14.3 |
| 20.480 | 4.3330 | 72.2 |
| 20.600 | 4.3080 | 71.6 |
| 20.720 | 4.2833 | 100.0 |
| 22.610 | 3.9294 | 25.5 |
| 24.470 | 3.6347 | 8.9 |
| 24.860 | 3.5786 | 13.5 |
| 25.190 | 3.5325 | 7.8 |
| 26.120 | 3.4088 | 5.7 |
| 26.600 | 3.3483 | 5.9 |
| 27.050 | 3.2936 | 3.5 |
| 27.530 | 3.2373 | 5.2 |
| 28.850 | 3.0921 | 6.7 |
| 29.090 | 3.0671 | 6.7 |
| 30.020 | 2.9742 | 4.0 |
| 30.320 | 2.9454 | 4.6 |
| 30.740 | 2.9062 | 5.6 |
| 31.220 | 2.8626 | 6.5 |

Definitions

The following terms shall have, for the purposes of this application, the respective meanings set forth below:

"Epothilone B comparative production conditions." To measure relative production of epothilone B to epothilone A, or net epothilone B production between strains, standard conditions are needed. The "epothilone B comparative production conditions" are set forth below. Note that standard conditions may be appropriately scaled (e.g., to 125 mL production flasks according to Example 2) as described in the Examples:

1) F1 Stage:

One mL from a frozen vial or maintenance flask is transferred to a 125 mL flask containing ca. 10 mL Medium E (composition described below). The F1 flask is incubated for 3–4 days at 30° C. and 160 rpm.

2) F2 Stage:

The entire contents from the F1 flask (ca. 10 mL) are transferred (10%) to a 250 mL flask containing 90 mL Medium E. This F2 flask is similarly incubated for 3–4 days at 30° C. and 160 rpm.

3) Production Stage:

Production flasks (250 mL flasks containing 90 mL Medium E, see medium formulations below) are inoculated at a level of 10% (10 mL) from the F2 stage. Alternatively, "maintenance flasks" may be used, and these are derived from routine flask transfer of culture every 3–4 days at levels ranging from 5% to 10%. The production phase incorporates at least 15 g/L of resin. Once inoculated, production flasks are incubated at 30° C. and 160 rpm for 14 days. A feed is incorporated to improve the epothilone B to A ratio. Feed additions begin at 72 hours post-inoculation as follows:

One mL of feed is added per production flask (100 mL culture volume) per day from days 3–11 with additions also continuing through day 14 where indicated.

The propionate-containing feed contains 10% Maltrin-M040, 4% sodium propionate, and 3% Tastone-154, such that when added as described at a 100-fold dilution, the final concentration in the culture broth, per day, becomes 0.1% Maltrin-M040, 0.04% sodium propionate, and 0.03% Tastone-154 (excluding residual levels from prior additions). Flasks were generally harvested for assay 14 days post-inoculation.

"Propionic acid precursor" refers to any compound that can be added to an appropriate culture in an amount effective to generate an amount of propionic acid effective to increase the epothilone B to epothilone A ratio. Propionic acid can be generated spontaneously, for example, with labile esters through the action of cellular enzymes. Those of ordinary skill in the art shall recognize candidate compounds which can be readily tested for generating propionic acid or for increasing the epothilone B to epothilone A ratio. Examples include methyl and ethyl esters of propionic acid.

By "feeding," it is meant that at least one or more nutrients or additives, such as propionate, sodium propionate, a sodium propionate containing mixture or solution, a vitamin, a mineral, a carbohydrate source or an amino acid source, is added on more than one occasion during the course of the fermentation, such as, for example, periodically, via a pulse feed, via a substantially continuous feed, and the like. It should be understood that a continuous feed throughout the fermentation is included within the meaning of the term "added on more than one occasion."

"Toluene-containing" means a solvate predominantly containing an amount of toluene as measured by analytical techniques used by those skilled in the art, wherein the toluene-containing solvate may or may not also contain one or more additional solvents.

"Ethyl acetate-containing" means a solvate predominantly containing an amount of ethyl acetate as measured by analytical techniques used by those skilled in the art, wherein the ethyl acetate-containing solvate may or may not also contain one or more additional solvents.

EXAMPLES

The examples below are carried out using standard techniques that are well known and routine to those of skill in the art, except where otherwise described in detail. The examples are illustrative, but do not limit the present invention.

Example 1

Preparation of the Strain SC16408 by Means of Mutation and Selection, and Preparation of Cell Banks Strain SC16408 was derived from the nitrosoguanidine (NTG) treatment of strain So ce90B2 (SC16224), followed by random selection. Thus, SC16224 was suspended in 10 mM Tris-HCl buffer and subjected to 1 mg/mL NTG for 60 minutes at pH 8.2. After treatment with NTG, colony cell lines were obtained by colony selection and tested for epothilone B productivity, and B/A ratio. Isolated colonies were transferred to flasks and cultured for 8–14 days, followed by transfers every 3–4 days in the growth medium (medium E):

Growth Medium E for shake flasks:

| Ingredient | g/L |
|---|---|
| Powdered Skim Milk | 4 |
| Toasted Nutrisoy Flour | 4 |
| Tastone-154 | 2 |

-continued

| Ingredient | g/L |
|---|---|
| Maltrin-M180 | 10 |
| CaCl$_2$.2H$_2$O | 1 |
| MgSO$_4$.7H$_2$O | 1 |
| EDTA, FeIII, Na salt | 0.008 |
| HEPES | 12 |
| Glycerol | 4.3 |

The above ingredients are added to distilled water and the pH is adjusted to pH 7.2 with 10% NaOH (or KOH) before sterilization for 30 minutes at 121° C.

Preparation of research cell bank: a volume of 10 mL from a 3-day old culture of strain SC16408 was transferred into a 250 mL flask containing 90 mL of medium E. The flask was then incubated at 30° C., 160 rpm for 2 days. At the end of 2 days, 1.8 mL aliquots were withdrawn from the flask and transferred into cryogenic vials, which were then frozen at −70° C.

Preparation of master cell bank: 2 vials from the research cell bank were thawed and transferred into 2×125 mL flasks containing 10 mL of medium E, and then incubated at 30° C., 160 rpm for 4–5 days. Next, 2×10 mL were transferred into 2×250 mL flasks containing 90 mL medium E and incubated at 30° C., 160 rpm for 2–4 days. Finally, these 2 flasks were pooled and 1.8 mL aliquots were transferred into cryogenic vials and stored in a freezer at −70° C.

Preparation of working cell bank: 5 vials from the master cell bank were thawed and transferred into 5×125 mL flasks containing 10 mL of medium E, then incubated at 30° C., 160 rpm for 3–6 days. Next, 5×10 mL were transferred into 5×250 mL flasks containing 90 mL medium E and incubated at 30° C., 160 rpm for 2–4 days. Cells in these 5 flasks were used to inoculate 12×250 mL flasks containing 90 mL medium E which were again incubated at 30° C., 160 rpm for 2–4 days. Finally, these flasks were pooled together and 1.8 mL aliquots were transferred into cryogenic vials and stored in a freezer at −70° C. About 500–600 vials were generated for this working cell bank.

Example 2

Cultivation to Produce the Epothilones by Shake Flask Fermentation

Cells from a frozen vial (1.5 mL) are inoculated into 45 mL of medium E in a 125 mL flask and grown for 4–8 days at 30° C. and 160 rpm (F1 stage). Then, 5 mL of the F1 stage are transferred to a new 125 mL flask containing 45 mL medium E and grown for 3–4 days (F2 stage). F2 stage cells are then used as inoculum for epothilone B fermentations. Ten percent of inoculum (5.0 mL) is transferred into a 125 mL flask containing 45 mL production medium. The flasks are then incubated in a shaker (160 rpm) at 30° C. for 2 weeks. The production medium is modified medium E, which contains 1.6% (0.8 g) XAD-16 resin. The composition of the production medium for shake flasks is shown:

Epothilone B production medium for shake flasks:

| Ingredient | g/L |
|---|---|
| Powdered Skim Milk | 4 |
| Toasted Nutrisoy Flour | 4 |

-continued

| Ingredient | g/L |
|---|---|
| Tastone-154 | 2 |
| Maltrin-M040 | 10 |
| CaCl$_2$.2H$_2$O | 1 |
| MgSO$_4$.7H$_2$O | 1 |
| EDTA, FeIII, Na salt | 0.008 |
| HEPES | 12 |
| Glycerol | 10 |
| XAD-16 resin | 16 |

The above ingredients are dissolved in distilled water and the pH is adjusted to 7.2 with 10% NaOH (or KOH) before sterilization for 30 minutes at 121° C.

The composition of feed solution for the shake flask epothilone B fermentation is: 4% sodium propionate, 10% Maltrin-M040 and 3% Tastone-154. The feed (100 mL in a 250 mL flask) is adjusted to pH 6.8–7.0 with NaOH and sterilized for 30 minutes at 121° C. From day 3 to day 14 post inoculation, 0.5 mL of feed solution is added daily to each fermentation flask. Alternatively, it has been found that comparable results may be achieved by doubling the feed levels and performing the additions at days 3, 5, 7 and 10. Improved results can also be achieved by further supplementing the above feed solution with phosphate, in the form of 1.5% dibasic sodium phosphate and 0.5% monobasic sodium phosphate, such that when diluted 100-fold into the culture medium, final levels are 0.015% and 0.005%, respectively, excluding residual levels from prior additions. An added advantage of phosphate addition is that no pH adjustment needs to be performed. Additional yield improvements (in epothilone B) as high as 10–20% can be achieved through phosphate supplementation.

For assay of epothilones, resin samples (0.8 g) are harvested and assayed by HPLC. Epothilone production in shake flasks should yield the following titers at 14 days:

Epothilone A: 5.0–7.0 mg/g resin
Epothilone B: 8.0–12.0 mg/g resin
B/A ratio: 1.1–2.0

Compared to previous strains, the SC16408 culture appears to produce more epothilone B in shake flasks.

Example 3

Cultivation to Produce the Epothilones in 14 L Fermentors

| | |
|---|---|
| F1 stage: | a 3.0 mL aliquot from two frozen vials is inoculated into 90 mL of medium E in a 250 mL flask and grown for 4–8 days at 30° C. and 160 rpm. |
| F2 stage: | 20 mL (10%) F1 stage cells are transferred to 180 mL of medium E in a 500 mL flask and incubated for 2–4 days at 30° C. and 160 rpm. |
| F3 stage: | Repeat F2 stage to increase inoculum quantity. Transfer 20 mL of inoculum from F2 stage into 6–8 × 500 mL flasks each containing 180 mL of medium E, and incubate flasks for 2–4 days at 30° C. and 160 rpm. |
| F4 stage: | Transfer 120 mL (10%) from F3 stage to 1080 mL of medium E in a 4 L aspirator bottle, then incubate for 2–4 days at 30° C. and 160 rpm. |

Medium E is used to build up the inoculum for a 14 L fermentor. The autoclave times for shake-flask and aspirator-bottle stages are 30 and 60 minutes, respectively. For the fermentor, the production medium is sterilized for 60 minutes at 121° C. The 14 L fermentor production medium is a modified shake flask production medium (as described above) where HEPES has been deleted and 2.5 g/L of an antifoam agent (Antifoam AF, from Dow Corning) has been added. Six liters of production medium (pH adjusted to 7.2–7.4) is dispensed in a 14 L fermentor and sterilized. The table below summarizes the process parameters at the 14 L fermentor scale:

Bench top fermentor process parameters:

|  | F1 to F4 | 14 L |
|---|---|---|
| Temperature | 30° C. | 32° C. |
| Pressure |  | 10 psi |
| Airflow |  | 0.25 vvm |
| pH |  | 7.2–7.4 |
| DO |  | 20–40% |
| Impeller diameter (in) |  | 3.3–4.2 |
| Tip speed (m/s) |  | 1.3–2.2 |
| Feed sterilization time |  | 60 min |
| Media sterilization time | 30 min | 60 min |
| Resin |  | 15–30 g/L |
| Nutrient feed composition: |  | A solution composed of 4.1% Maltrin-M040 and 1.3% Tastone-154 is prepared in a 5 L bottle. The feed is sterilized for 60 minutes at 121° C. |
| Nutrient feed rate: |  | The feed rate is 6 mL/hour. |
| Sodium propionate feed: |  | 5.0% sodium propionate (1.5 L in 2 L bottle) is sterilized for 60 minutes at 121° C. |
| Sodium propionate feed rate: |  | From 24–48 hours to finish, 2 mL/hour. The feed rate is adjusted to maintain sodium propionate concentration between 0.05–0.2 mg/mL based on HPLC assay. |

The epothilone B titer range in 14 L fermentors is summarized below:

| Epothilone B titer, mg/g resin | B/A Ratio |
|---|---|
| 5–12 | 1.0–3.0 |

Example 4

Manufacturing Process for Epothilones

50 L Fermentor Seed Stage:

For the F1 stage, medium E (2 L) is made up and dispensed, 90 mL each into 17 separate 250 mL flasks. The flasks are then sterilized by autoclaving at 121° C. for 30 minutes. Cells from one frozen vial are inoculated into each flask and grown for 4–8 days at about 30° C. and 160 rpm.

For the F2 stage, 27 L of medium E are made up and dispensed, 1.5 L each into 17 separate 4 L flasks, then sterilized as above. Each 4 L flask is inoculated with the entire contents of a flask from the F1 stage, then grown for 2–4 days at about 30° C. and 160 rpm.

For the F3 stage, 80 L of medium E* is made up and divided into two 50 L stainless steel seed fermentors and each 50 L fermentor is inoculated with the contents of three 4 L flasks from the F2 stage. The 50 L fermentors are grown for 2–4 days at 30–33° C., then combined and used to inoculate an 800 L fermentor.

Medium E* is:

| Ingredient | g/L |
|---|---|
| Powdered Skim Milk (or soy protein concentrate) | 5 |
| Toasted Nutrisoy Flour | 5 |
| Tastone-154 | 2.5 |
| Maltrin-M040 | 12.3 |
| $CaCl_2.2H_2O$ | 1.2 |
| $MgSO_4.7H_2O$ | 1.2 |
| EDTA, FeIII, Na salt | 0.012 |
| Glycerol | 5.4 |
| Antifoam | 2.5 |

800 L Fermentor Seed Stage:

The inoculum is grown in an 800 L stainless steel fermentor until the cell mass is sufficient to inoculate the next seed stage (a 5,000 L fermentor).

Medium E* for the batch is made up into deionized water (400 L) and the mixture, pH 8.7–8.9, is sterilized at 17 psig, 124° C. for 60 minutes. The medium is transferred from the sterilizer to the 800 L fermentor, and pH adjusted to pH 7.1–7.3. The fermentor is then inoculated with 80 L from the F3 stage. The batch is run with the following control set points:

| Pressure: | 8–12 psig | Air Flow: | 0.5–0.7 vvm |
|---|---|---|---|
| Temperature: | 30–33° C. | pH: | 7.1–7.3 |
| Agitator shaft speed: | 50–60 rpm |  |  |

As needed, caustic (sodium or potassium hydroxide solution) is added from a sterile supply to maintain pH in the 7.1–7.3 range. The batch is sampled at intervals and analyzed for sterility, pH, sediment and glucose concentration. Vent off-gas $CO_2$ and $O_2$ are also monitored. At approximately 48–60 hours, when the glucose concentration is starting to fall, the contents of the 800 L fermentor (approximately 440–480 L) are transferred to a 5,000 L fermentor.

5.000 L Fermentor Seed Stage:

A 5,000 L stainless steel fermentor is used in the inoculum process at this stage. The inoculum is grown in the fermentor until the cell mass is sufficient to inoculate the 40,000 L production fermentor.

Medium E*, prepared as above (into deionized water, 2,600 L), is transferred to the 5,000 L fermentor and then inoculated with approximately 440–480 L of inoculum from the 800 L fermentor. The batch is run with the control set points and monitoring described above. Again, pH is maintained in the 7.1–7.3 range. At about 48–72 hours, when the glucose concentration begins to fall, the contents of the 5,000 L fermentor are transferred to the 40,000 L fermentor.

40,000 L Fermentor Production Stage:

A 40,000 L stainless steel fermentor is used in the production of the epothilones. Once the fermentor has been sterilized and filled with sterile medium, it is inoculated with the seed prepared in the 5,000 L fermentor. Once specific production parameters are achieved, the contents of the production fermentor are harvested.

The medium for the production fermentor is sterilized in two parts. The resin is added into 2,800 L of water and the mixture is sterilized at 17 psig, 124° C. for 75 minutes:

| Ingredient | Amount |
| --- | --- |
| Washed XAD-16 Resin | 15–40 g/L |

To make 18,000 L of medium, the following ingredients are added into deionized water (15,000 L) and the pH is adjusted to 7.1–7.3. The medium is sterilized at 150° C. in a continuous sterilizer (hold time 100 seconds, outlet temperature 60° C.):

| Ingredient | Weight (kg) |
| --- | --- |
| Powdered Skim Milk | 130 |
| Toasted Nutrisoy Flour | 130 |
| Tastone-154 | 65 |
| Maltrin-M040 | 238 |
| $CaCl_2 \cdot 2H_2O$ | 21.6 |
| $MgSO_4 \cdot 7H_2O$ | 21.6 |
| EDTA, FeIII, Na salt | 0.22 |
| Glycerol | 216 |
| Antifoam | 54 |

The medium and resin are transferred to the production fermentor which is then inoculated with approximately 3,100 L of inoculum from the 5,000 L fermentor. The batch is run with the control set points described above, except air flow is 0.2–0.4 vvm. As needed, the pH (between 0 and 80 hours) is raised with caustic. After 80 hours, the pH is lowered with sulfuric acid. As needed, foaming is controlled with antifoam. The fermentor is sampled at least once a day for sterility, pH, sediment, glucose, propionate and epothilone B concentration. $CO_2$ in the off-gas is monitored and recorded. Feeds are started at approximately 30–60 hours, as long as the $CO_2$ is at least 0.3%.

The fermentor is fed sodium propionate (102 g/L) with a shot size of 1.9 L/shot (range 1.5–3.0). The interval between shots starts at 60 minutes and decreases every 12 hours to a minimum of 12 minutes. The propionate is added into 2,800 L of deionized water and the solution is sterilized at 17 psig, 124° C. for 75 minutes. In a preferred embodiment, the sodium propionate feed is separate from the feed containing other media components.

The fermentor is fed Maltrin-M040 and Tastone-154 with a shot size of 14.5 L. The interval between shots starts at 60 minutes and changes at 104 hours to 40 minutes. The ingredients are added to deionized water (3,000 L) and sterilized at 17 psig, 124° C. for 75 minutes. The feed comprises:

| Ingredient | g/L |
| --- | --- |
| Tastone-154 | 20 |
| Maltrin-M040 | 66 |
| Antifoam | 1.0 |

During the run, some of the medium components such as powdered skim milk, Maltrin-M040 and glycerol are exhausted. Starting at approximately 115 hours, the previous feed is discontinued and the following mixture with a shot size of 14.5 L is added to the production fermentor at intervals of 40 minutes. The ingredients are added into deionized water (3,000 L) and the mixture, pH 8.7–8.9, is sterilized at 17 psig, 124° C. for 75 minutes:

| Ingredient | g/L |
| --- | --- |
| Powdered Skim Milk | 49 |
| Maltrin-M040 | 154 |
| Tastone-154 | 20 |
| Glycerol | 78 |
| Antifoam | 1.6 |

When a desired epothilone B concentration is achieved (normally after 9–21 days), the contents of the vessel are harvested. Epothilone B titers range from approximately 5–24 mg/g Resin, with B/A ratios from approximately 1.5–4.

Example 5

Extraction of Epothilone B from XAD-16 Resin with MTBE and Crystallization to Give Solid Epothilone B; Purification by Reverse Phase Chromatography; and Final Isolation of High-quality Epothilone B Harvested and water-washed XAD-16 resin (approximately 550 kg) containing epothilones (approximately 5.03 kg epothilone B) is mixed with aqueous methanol and loaded into an extraction column as a slurry. The packed resin is washed with aqueous methanol (1 bed volume each of 30% then 50% MeOH) to remove highly polar undesired materials. Epothilones are removed with MTBE washes (approximately 4 bed volumes). The rich eluate is collected and polish filtered. After gravity settling to remove any aqueous phase, the rich MTBE is concentrated. The concentrate is gravity settled, the aqueous phase removed, and additional MTBE (2 bed volumes) added to the batch. The batch is re-concentrated to a concentration of approximately 5 to 15 g epothilone B per L. The batch is crystallized by gradual cooling over 5–6 hours at approximately 0° C. The crystalline solid is filtered, washed and dried. The resulting product cake is dissolved in warm ethyl acetate and polish filtered. The rich filtrate is concentrated under vacuum to a concentration of approximately 20 to 45 g epothilone B per L. After heating to 70° C., the batch is then cooled slowly to approximately 0° C. to give a crystalline slurry which is filtered, washed with cold EtOAc, and dried at less than 40° C. to give isolated recrystallized epothilone B (in 84% yield from the resin). This product is then purified by reverse phase chromatography.

A chromatographic column (11 cm diameter×40 cm bed length) packed with reverse phase stationary support RP/C-18 is equilibrated with aqueous acetonitrile (30–50% v/v). Recrystallized product is dissolved in dimethyl sulfoxide (DMSO, 1–1.5 L per kg), the mixture filtered to remove insoluble materials, then loaded onto the column preceded by an aliquot of 100% DMSO, and chased by an equal volume of DMSO to reduce precipitation of the sample upon introduction of the aqueous mobile phase. The sample is eluted from the column using aqueous acetonitrile (30–50% v/v), and the effluent is monitored at 290 nm by a UV detector. The epothilone B product peak is collected in a number of fractions. The fractions are assayed by HPLC for both epothilone A and B and other related impurities.

Desired pooled column fractions are charged to a distillation package, and the batch vacuum-concentrated to remove the acetonitrile at a temperature below 40° C. The resulting aqueous phase is extracted up to three times with ethyl acetate, and the organic solution is concentrated under vacuum at a temperature below 40° C. to give a concentration of 0.1 to 0.2 g/mL of epothilone B. n-Heptane (or heptanes) is added to the batch at 40° C., then the batch is cooled slowly to 2 to −10° C. and held for at least 2 hours. The crystal slurry is filtered and washed with an ethyl acetate/n-heptane solution, then the final epothilone B cake is dried under vacuum at 35–40° C. to yield 3.367 kg with a potency of 91.7% equivalent to 3.09 kg of epothilone B activity. The yield from the resin was 61.4%. HPLC indicated 99.6 area % epothilone B, 0.4 area % epothilone A, with no other impurity present at >0.1 area %.

Example 6

Extraction of Epothilone B from XAD-16 Resin with Ethyl Acetate and Crystallization with Toluene as Antisolvent to Give Solid Epothilone B; Purification by Reverse-Phase Chromatography; Final Isolation of High-quality Epothilone B XAD-16 resin containing epothilone B is washed with water on a vibrating screen (SWECO TM) to clean the resin. A portion of this (approximately 6.6 L, containing 15.6 g epothilone B, assay 2.36 mg of epothilone B per gram of resin) is transferred to a 20 L container using approximately 5 L of water to rinse the resin with water. Ethyl acetate (approximately 2 bed volumes (BV) of input resin) is then added to the container. The slurry is stirred for about one hour, and centrifuged at 3,500 rpm for 5 minutes using 600 mL screw cap centrifuge jars to separate layers. The first rich ethyl acetate supernatants are decanted, and their volumes are measured. Next, the lean aqueous resin-containing bottom layers are pooled in the container, and ethyl acetate(2 BV) is added to the container. The slurry is stirred for about 1 hour and then centrifuged to separate layers. The second rich ethyl acetate supernatants are decanted, and their volumes are measured.

Water (~0.3 BV of input resin) is then added to the combined rich first and second ethyl acetate streams and agitated for approximately 5 minutes. Layers are permitted to settle for approximately 30 minutes. Next, the lower aqueous layer is separated from the upper rich ethyl acetate layer. The rich washed ethyl acetate layer is concentrated at a temperature less than 45° C., to a concentration of approximately 10 g of epothilone B activity per liter. The concentrated rich ethyl acetate solution is then polish filtered and concentrated to 20–25 g/L of epothilone B.

After concentration, toluene is added and the batch is re-concentrated using vacuum at less than 50° C., to the volume of the batch before toluene addition. The batch is allowed to cool to about 18° C. over approximately 1 hour, then stirred for approximately 16 hours at this temperature to produce product crystals. Next, the crystallization batch is filtered and washed with toluene (~0.2 BV) and the solids are dried to yield approximately 30.4 g of solid containing 13.5 g of epothilone B activity. The activity yield from starting resin is 87%.

Purification by reverse-phase chromatography is performed on the solid epothilone B extracted from resin using the above process. The column (Phenomenex Luna, 15, C18(2), 5.0 cm×25 cm, column BV 400 mL) is pre-equilibrated with 3 BV of 40% (v/v) acetonitrile-water. Approximately 4–6 g of the solid epothilone B is dissolved in approximately 6 mL of DMSO at about 40° C., then the mixture is filtered through filter paper to remove particulates. Approximately 1.5 mL of DMSO is injected into the sample loop to prevent precipitation of epothilones in the tubing. The epothilone-rich filtrate is then injected into the sample loop. Following the injection, the epothilone filtrate container is washed with around 0.5 mL of DMSO and injected along with about 1 mL of DMSO into the sample loop. Injection of DMSO after injection of the epothilone sample prevents precipitation in the tubing. The contents of the sample loop are loaded onto the column at a flow rate of approximately 5 mL/min.

After loading the epothilone onto the column, the 40% acetonitrile-water solution is then pumped through the column. After 3–4 minutes, the flow rate is increased to approximately 60 mL/min. The epothilone A and B peaks are collected in fractions. The rich epothilone B-containing fractions typically are obtained in the cuts between about 2.5 L and 3.25 L eluted volume (the epothilone B peak typically elutes between about 6 and 8 bed volumes). The volume of the pooled fractions is approximately 0.75 L. After the peak for epothilone B has nearly reached baseline (<10% of peak height), 100% acetonitrile is pumped through the column. When the chromatogram indicates that the absorbance at 290 nm has essentially returned to baseline, re-equilibration of the column is initiated for the next run by pumping 40% acetonitrile-water solution onto the column. Typically 2 BV of 100% acetonitrile and 3 BV 40% acetonitrile are used to wash and re-equilibrate the column.

Fractions are assayed to determine purity using HPLC analysis, and the desired fractions pooled. Typical yields are 90–98%.

The pooled epothilone B fractions are concentrated under vacuum at less than 40° C., to approximately 50% of initial volume. The concentrated fractions are extracted with ethyl acetate. The pooled ethyl acetate extracts are concentrated to approximately 0.1 g/mL epothilone B at a bath temperature of approximately 40° C. While stirring, n-heptane (or heptanes) (using a volume of 50% of the ethyl acetate solution) is added over a period of about 15 minutes. Extracts are cooled to 5° C. and held at that temperature for at least 2 hours. The product crystals are filtered and washed with a 1:2 (v:v) n-heptane:ethyl acetate solution. Finally, crystals are dried under vacuum at approximately 40° C. for approximately 12 hours. HPLC indicated, for various batches. 99.5–99.7 area % epothilone B, and 0.3–0.5 area % epothilone A.

Example 7

Extraction of Epothilone B from XAD-16 Resin with Ethyl Acetate and Crystallization with Toluene as Antisolvent, Followed by Recrystallization to Give Primary Grade Epothilone B; Purification by Normal-Phase Chromatography; and Final Isolation of High-Quality Epothilone B Step A, Preparation of Primary Grade Epothilone B Using EtOAc Extraction-toluene Crystallization:

Water washed epothilone B rich resin (1350 g) is loaded onto a column. Water (2700 mL) is used to load and rinse the column. The epothilone activity is eluted by passing 9450 mL (7 bed volumes) of ethyl acetate through the column. The ethyl acetate eluate is allowed to settle for at least one hour. A dark brown aqueous layer and an emulsion layer are removed. The rich ethyl acetate solution is concentrated under vacuum to a target concentration of approximately 20 g of epothilone B per L. The concentrate is allowed to stand 2 hours and cooled to 20° C. The cooled concentrate is polish filtered, and the filter washed with ethyl acetate (36 mL). The combined filtrate and wash are concentrated to approximately 80 g epothilone B per L and heated to 65° C. An equal volume of toluene is added with stirring over 10–15 minutes while keeping the temperature above 60° C. The temperature is maintained at 65° C. for 30 minutes followed by lowering the temperature to 40° C. over 1.5 hours and then lowering the temperature to 1° C. over 2 hours. The resulting crystalline slurry is stirred at 1° C. for at least 60 minutes. The solids are filtered off and washed with toluene (20% of the slurry volume). (In various repetitions of this method, the mother liquor typically contains 2–6% of the input epothilone B activity). The solids are dried in a vacuum in an oven at 40–45° C. for at least 4 hours. Alternatively, the solids are dried in a vacuum in an oven at a temperature between about 40° C. and room temperature for at least 4 hours.

The dry primary epothilone B cake weight ranged from 8.4 to 20 g, the epothilone B potency ranging from 650 to 713 µg/mg. The cake also contained 12% to 26% epothilone A (area percent). The residual solvent levels were 0.7% (w/w) EtOAc and 13% (w/w) toluene.

For five lots that were evaluated:

| Weight input (g) | assay (g epo B/Kg) | epo B input (g) | Epo B in Primary cake (g) | % recovery |
|---|---|---|---|---|
| 1327–1391 | 4.4–12.2 | 6.0–16.5 | 5.5–13.6 | 87–98 |

The total losses for the isolation process averaged 9.4%. The percent of the epothilone A peak relative to the epothilone B peak from resin to primary cake dropped from an average of 49% to 19%. The PXRD pattern and thermal analysis for crystal solvate obtained following the method described in this step are set forth in FIGS. 9 and 10, respectively. The PXRD pattern of FIG. 9 is further characterized by the data reported in Table 6, above.

Step B. Recrystallization of Epothilone B:

EtOAc (0.14 L) is added to 15 g primary grade epothilone B (710 µg/mg) and heated to 65–68° C. with stirring. (The target concentration of epothilone B was 75–80 g activity per liter). Toluene (0.14 L) is added over 20 minutes while maintaining a temperature above 60° C. The resulting slurry is held at 65° C. for 0.25 hours to 1 hour. The batch is then cooled to 40° C. over 3 hours. Cooling of the batch is continued to 0–2° C. over 2 hours. The batch is then held at 0–2° C. for 12 hours. The resulting crystalline slurry is then filtered and the cake washed with toluene (2×0.028 L). Typically, less than 3% of the input epothilone B activity is lost to the combined mother liquor and wash. The cake is dried in a vacuum oven at 42° C. and 29 in. Hg for 2 hours. Alternatively, the cake is dried in a vacuum oven at a temperature between about 40° C. and room temperature and 29 in. Hg for 2 hours. The dry cake weight is 13.6 g with a potency of 764 µg/mg. Residual solvents include EtOAc (0.9 wt %) and toluene (13.2%). Typically, EtOAc and toluene are present at combined levels of 13–14 wt %. The percent of the area of the epothilone A peak relative to the epothilone B peak for recrystallized cake dropped to an average of 6.9%.

Figure 12:
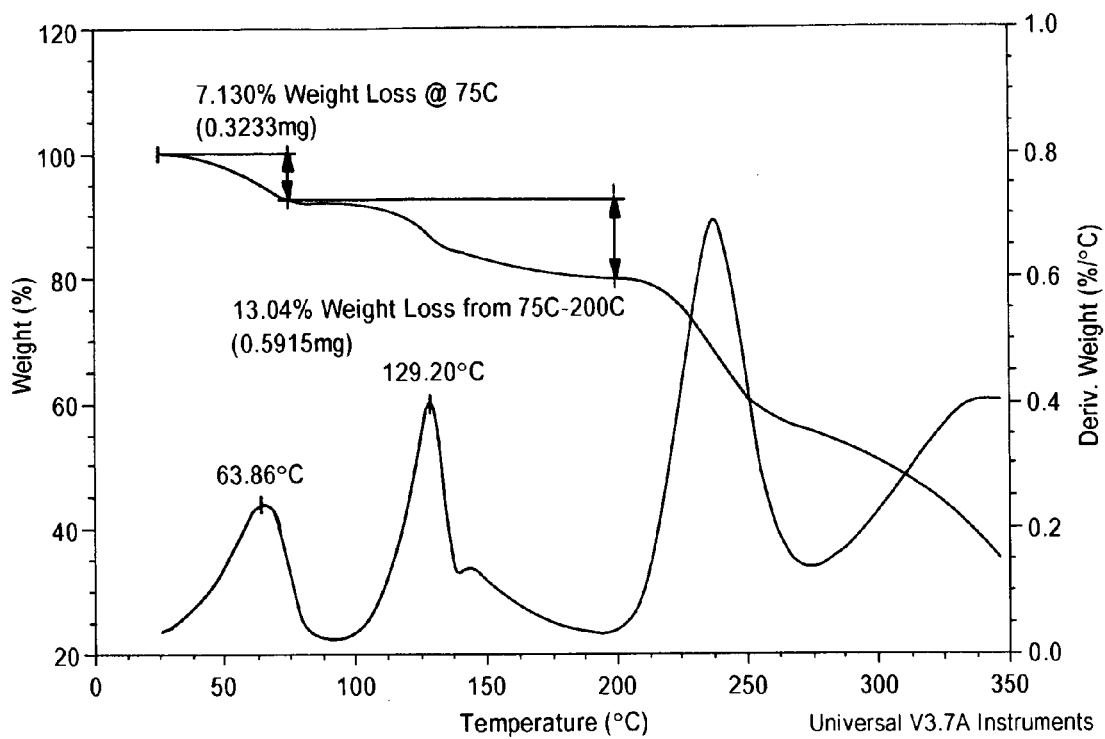
FIG. 12 shows the thermal analysis (DSC and TGA) for the toluene-containing recrystallized solvate of FIG. 11.
Figure 12:
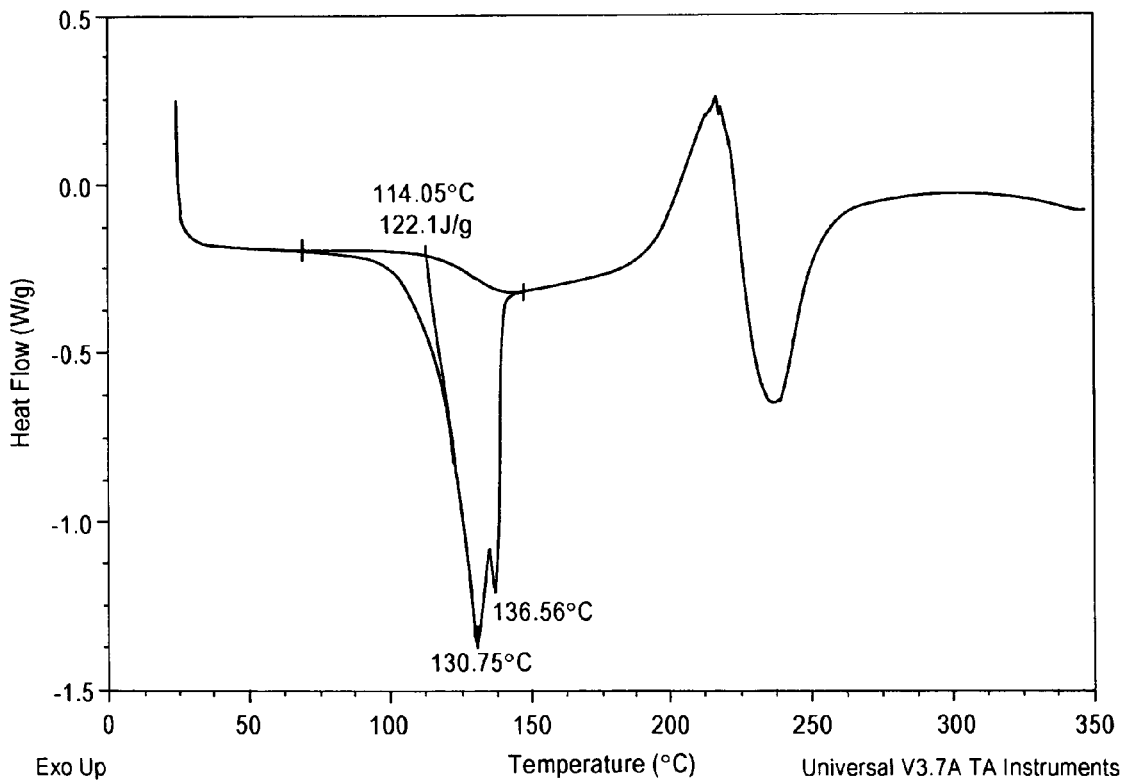

The PXRD pattern and thermal analysis for crystal solvate obtained following the method described in this step are set forth in FIGS. 11 and 12, respectively. The PXRD pattern of FIG. 11 is further characterized by the data reported in Table 7, above.

Normal Phase Chromatography:

The following mobile phases are prepared:
20% (v/v) ethyl acetate/n-heptane solution (~10 L),
40% ethyl acetate/n-heptane (~10 L), and
100% ethyl acetate (~10 L).

The following equipment is set up:
Waters Delta Prep 4000; Detector: UV set at 290 nm; Column: Phenomenex Luna, 10 micron, silica (2), 5.0 cm×25 cm (column volume~490 mL).

The column is equilibrated with 3 bed volumes of 20% (v/v) ethyl acetate/n-heptane solution prior to injection of the epothilone solution.

The epothilone B cake (5.5 g) is dissolved in 55 mL of methylene chloride. The batch is filtered through a 1-micron PTFE filter to remove any particulates that may be present. Methylene chloride (2–5 mL) is used to rinse the filter. The rich methylene chloride filtrate is injected onto the column at an initial flow rate of 5 mL/min for the first 30 seconds, followed by increasing the flow to 20 mL/min until the sample is fully loaded. The container containing the epothilone filtrate is rinsed with methylene chloride (2–5 mL), and the rinse is also loaded onto the column.

The elution is begun with 20% EtOAc/heptane while increasing the flow rate to 118 mL/min. After the flow rate reaches 118 mL/min, the pump program controller is used to run the desired pump program. The following pump program is used:

| Time | flow (mL/min) | % ethyl acetate/heptane A | B | C | volume mL | bed volumes BV |
|---|---|---|---|---|---|---|
| 0 | 118 | 20 | | | | |
| 7.5 | 118 | 20 | | | 897 | 1.83 |
| 7.6 | 118 | | 40 | | | |
| 45.6 | 118 | | 40 | | 4496 | 9.18 |
| 45.7 | 150 | | | 100 | | |
| 69.3 | 150 | | | 100 | 3555 | 7.26 |
| 69.4 | 150 | 20 | | | | |
| 85.7 | 150 | 20 | | | 2460 | 5.02 |
| 85.8 | 0 | 20 | | | | |

Fractions are collected and assayed for purity using HPLC.

In five batches, the area percent of epothilone B in the collected fractions was 99.59–99.93%, with yield averaging 91%.

Optionally, the chromatography is performed similarly using an isocratic 40% ethyl acetate/n-heptane elution step, with the similar 100% ethyl acetate column washing step followed by re-equilibration with 40% ethyl acetate. The same chromatography equipment is used with a smaller diameter column 1.0 cm×25 cm. The chromatography yield for epothilone B (164 mg) in the heartcut fractions was 86% and the area percent of epothilone B in the collected fractions was 99.4%. The above isocratic process was also performed on an 11 cm axial compressed column with 31–35 gm of epo B eluted in the heartcut with chromatographic yields of 90–94%. The area percent of epothilone B in the collected heartcuts was 99.6–99.9%. The column can be re-used multiple times.

Figure 14:
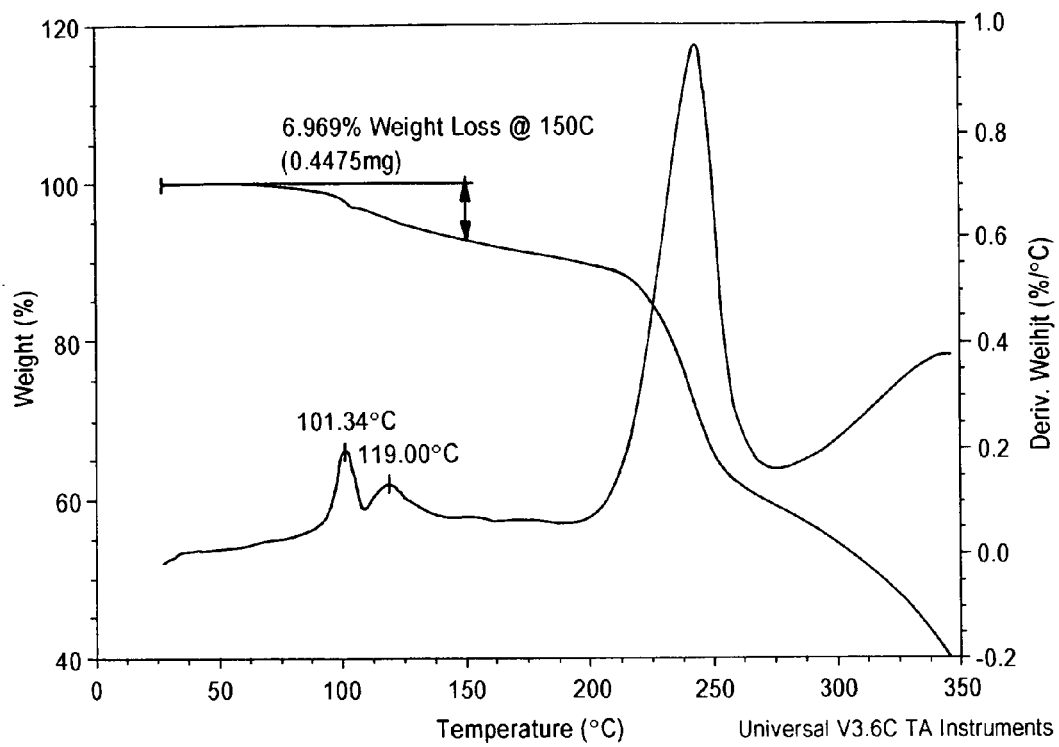
FIG. 14 shows the thermal analysis (DSC and TGA) for the ethyl acetate containing solvate of FIG. 13.
Figure 14:
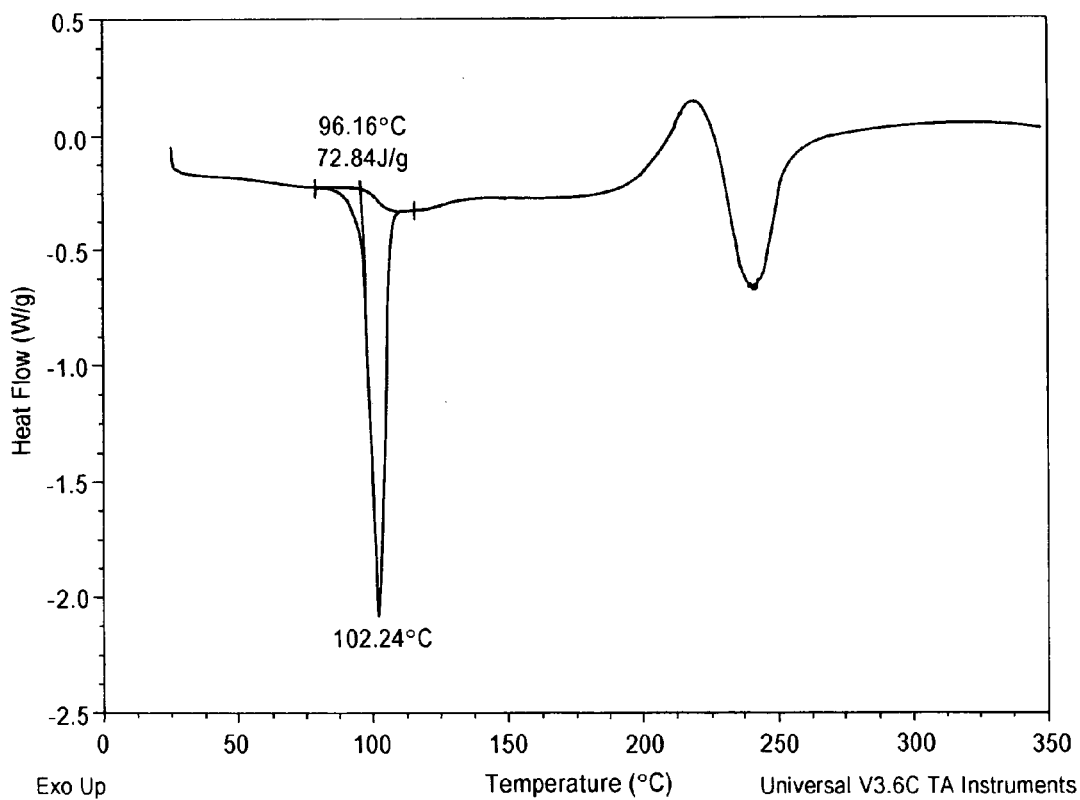

Step C, Final Crystallization:

The desired heart-cut fractions are pooled together to give a batch volume of 1.62–1.73 L. The solvent is removed under vacuum at 40–45° C. The target distillation volume is 25–28 mL (epothilone B concentration of approximately 200–210 g/L). To the concentrate is added warm (approximately 40° C.) heptane (50 mL). Alternatively, warm (approximately 40° C.) EtOAc (50 mL) could be added to the concentrate at this step. The resulting slurry is stirred at approximately 40° C. for about 2 hours, then is cooled to approximately 0° C. over about 5 hours and is further stirred at approximately 0° C. for a minimum of 5 hours. Mechanical stirring at moderate rate is used throughout the crystallization. The crystalline slurry is filtered and the cake is washed with cold 1:1 EtOAc/heptane (25 mL). The solids are dried in a vacuum oven at 40–45° C. for 5–6 hours. Alternatively, the solids are dried in a vacuum oven at a temperature between about 40° C. and room temperature for 5–6 hours. The weight of isolated epothilone B (for five batches) is approximately 4.2–5.0 g (83.5–85.6% activity yield) from recrystallized (one time) epothilone B, and the HPLC purity is 99.78 to 99.93% area percent (average 99.80%). The epothilone B lost in the mother liquor is approximately 4% with respect to epothilone B activity input to chromatography. Residual solvents in the cake are EtOAc (5.8–6.0% w/w) and heptane (0.6–0.7% w/w). The potency of the final epothilone B cake ranges from 91.5 to 92.7% w/w. The HPLC purity is above 99.7 area percent. The PXRD pattern and thermal analysis for a crystal solvate obtained following the method described in this step are set forth in FIGS. 13 and 14, respectively. As can be seen in FIG. 14, the melting point for the ethyl acetate solvate prepared and dried according to the above procedure is approximately 102° C. The PXRD pattern of FIG. 13 is further characterized by the data reported in Table 8, above.

Alternatively, pooled heart cuts containing 4.83 Kg of Epo B (1790L) were concentrated under vacuum at <30° C. to a target concentration of 200–210 g/L and then n-heptane (60 Kg) was added. This concentration was repeated and then an additional 60 Kg of heptane was added. The slurry was cooled to 20° C. over three hours, then collected and washed with 30 Kg of heptane. The solids were dried at 20–36° C. for 16 hours under vacuum. A total of 5.141 Kg of solid were obtained with an HPLC purity of >99.6 area %. Residual solvents in the cake were 10.6% ethyl acetate and 1.4% heptane.

Example 7A

Extraction of Epothilone B from Resin, Followed by Repeated Recrystallization

Water washed epothilone rich resin (549.8 kg) containing an estimated 4.10 Kg of epothilone B activity (Area % for epothilone B=58.0%; epothilone A=29.2%) was slurried with water and charged to a column (700 L). The column was drained and blown with nitrogen. Ethyl acetate (2969 Kg) was then eluted through the column at a rate of ~1 bed volume per hour for a total of ~6 bed volumes. The combined rich ethyl acetate eluate was allowed to gravity settle for ~1 hour before removing the lower aqueous phase. The rich ethyl acetate was then concentrated to ~574 kg. The concentrated rich ethyl acetate was then allowed to stand at ~20° C. for ~2 days before polish filtering. The filter and lines were washed with ethyl acetate (~115 kg total). The polish filtrate and wash was then concentrated to a volume of ~64 L, then warmed to ~65° C. An equal volume of warm toluene was then added with stirring and the material was held at ~65° C. for ~30 minutes. The batch was then slowly cooled to ~40° C. over ~4 hours, followed by cooling to 0° C. over ~2.5 hours. The cold slurry was then held at ~0° C. for ~1 hour. The resulting crystalline slurry was then filtered and the cake washed with toluene. (~64 L). The resulting cake was dried briefly under vacuum then redissolved from the filter dryer using warm ethyl acetate (~200 kg).

The first recrystallization was performed similarly by concentrating the rich ethyl acetate to ~65 L. After warming to 65° C. an equal volume of toluene was added with stirring and the material was held at ~65° C. for ~30 minutes. The batch was cooled similarly as above and the resulting crystalline slurry was filtered and washed using the same procedure and equipment as above.

Two additional similar recrystallizations as described above were performed to yield an epothilone B crystalline cake with (4.384 Kg)(81.5% w/w) (3.573 kg epothilone B) (HPLC Area %'s for: epothilone B=97.18: epothilone A=1.40; epothilone F=0.30; oxazole analog=0.30 and ethyl thiazole analog=0.56). No other impurities were detectable by HPLC over 0.1 area percent. The product contained 13.8% w/w toluene and 0.8% w/w ethyl acetate. The overall activity yield from resin to isolated purified epothilone B was 87%.

Example 7B

Recovery of Epo B from Mother Liquor Streams

Mother liquors from the crystallization of Epo B from MTBE or EtOAc extracts were combined and contained 2.2 g of Epo B and 4.8 g of Epo A per liter of solution. Ten liters of this solution were concentrated under vacuum at $\leq 50°$ C. to a concentration of 11–15 g of Epo B per liter. One volume of toluene was added and solids began forming; distillation was continued until a concentration of 11–15 g Epo B/L was again achieved. One volume of toluene was added again and the distillation was repeated once more to reach 11–15 g Epo B/L. The slurry was cooled to room temperature over 1 hour, then stirred for 90 minutes. The mixture was then re-heated to ~50° C., stirred for 1 hour and cooled to room temperature over 1 hour. After stirring for a minimum of 3 hours, the solids were collected by filtration, washed with toluene and then dried under vacuum at ~40° C. to give a recovery of ~92% of Epo B activity. The solids assayed 42.9% w/w Epo B with 16% w/w toluene. The mother liquor contained 66% of the input epothilone A and only 5% of the input epothilone B.

Example 7C

Pooled heart cuts (200 mL), from the normal phase chromatography procedure set forth in Example 7, containing 646 mg of Epo B were slowly added to 43 mL of toluene while concentrating under vacuum with a jacket temperature of ~65° C. to ~43 mL. Toluene (43 mL) was added under vacuum while distillation continued with a jacket temperature of ~65° C. The slurry was concentrated to ~43 mL and was then allowed to cool to ~20° C. over ~3 hours The crystals were collected, washed with 2×5 mL toluene and dried under vacuum (2941 Hg) at ~40° C. for 30 minutes to give 729 mg of isolated crystalline cake (85.3% w/w Epo B). The HPLC purity was 99.77 area % (excluding toluene area %). Residual solvents in the cake were 15.3% w/w toluene and 0.3% w/w EtOAc. The mother liquor and wash contained only 0.5% of the epothilone B input activity.

Figure 15:
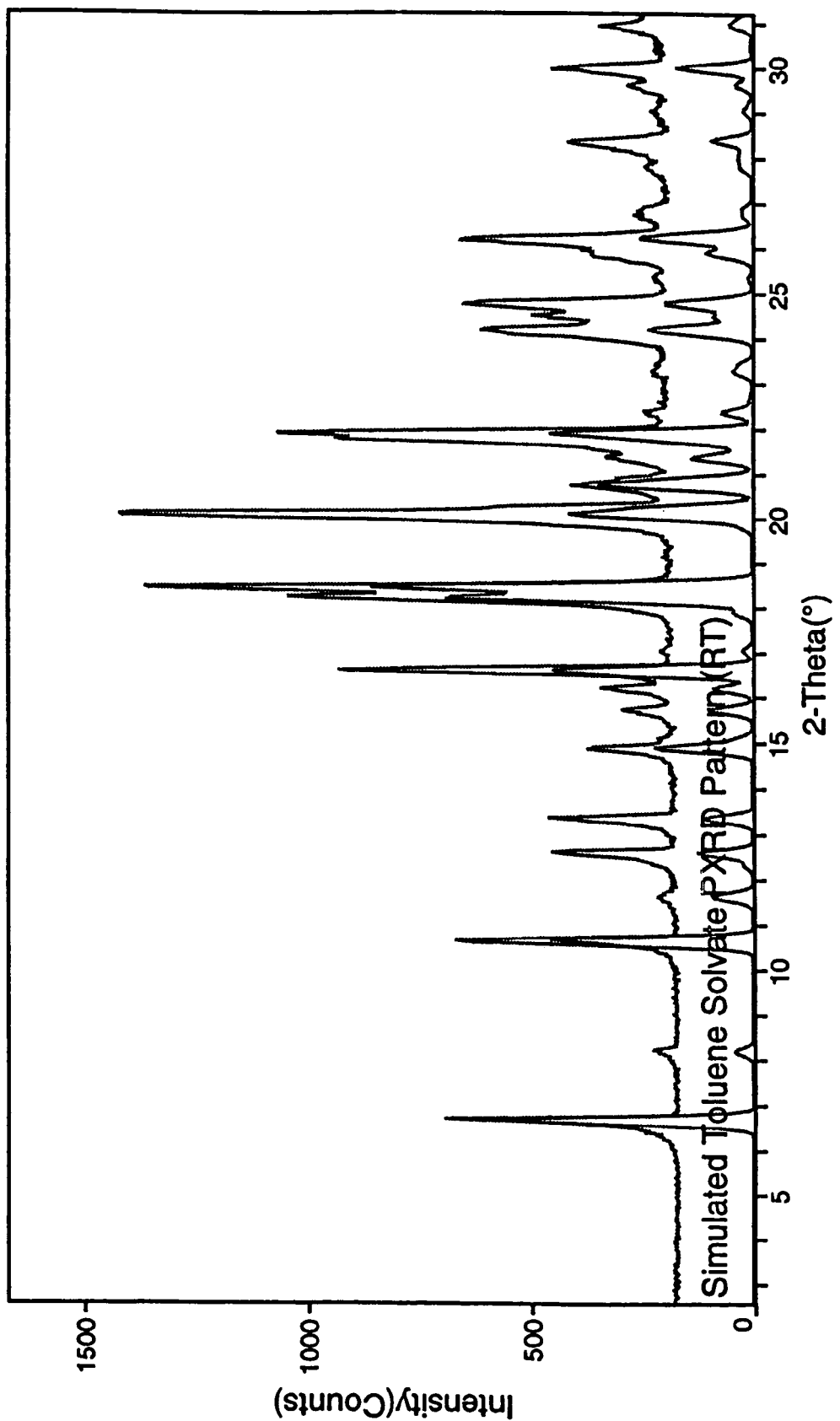
FIG. 15 shows an observed (top) PXRD pattern for the toluene-containing solvate prepared following the method described in Example 7C, together with a simulated (bottom) PXRD pattern for the toluene solvate of epothilone B at room temperature.
Figure 16:
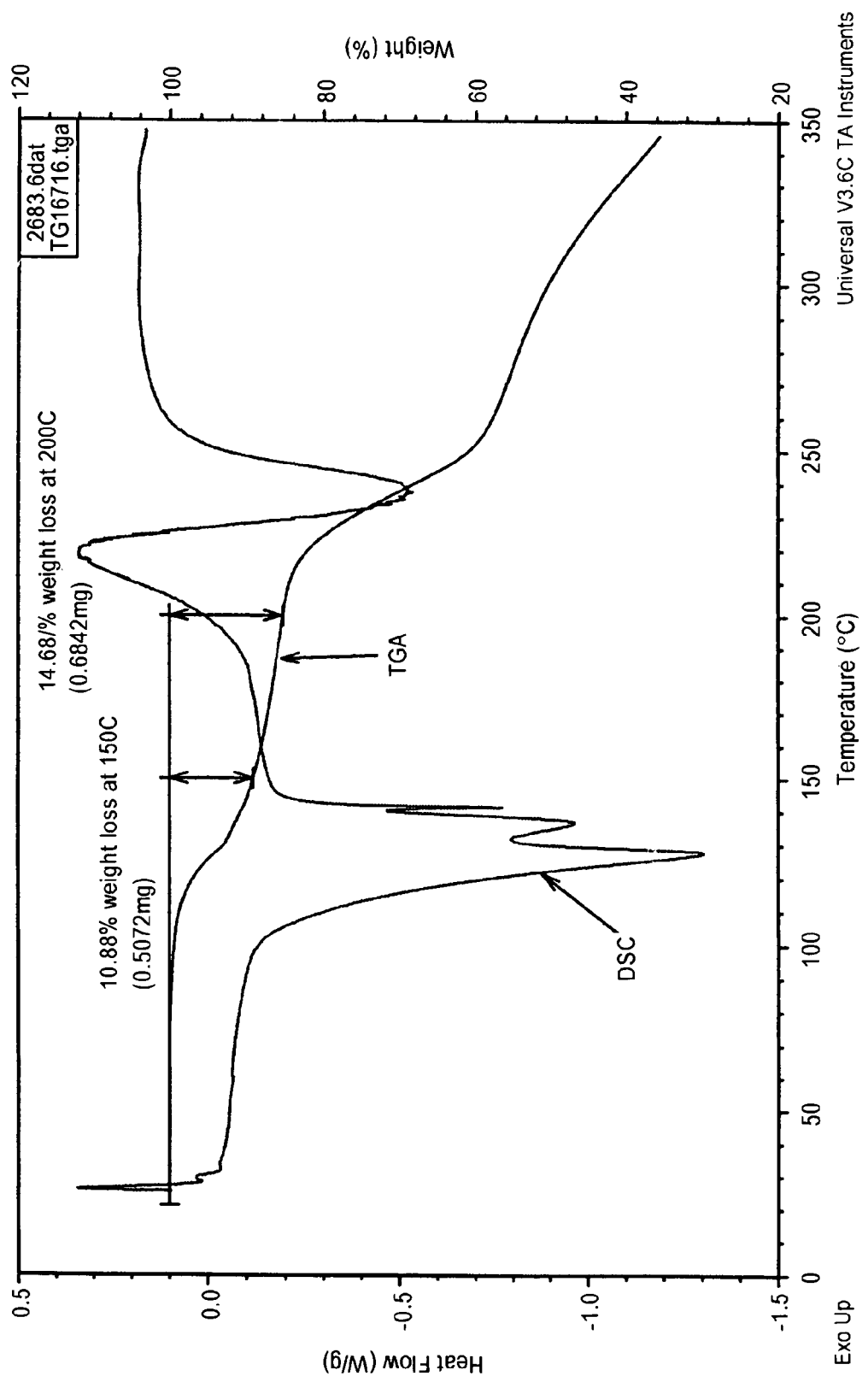
FIG. 16 shows the thermal analysis (DSC and TGA) for the toluene-containing solvate of FIG. 15.

An observed PXRD pattern for crystal solvate obtained following the methods described in this step is set forth in FIG. 15 (top pattern), along with a simulated PXRD pattern for a toluene solvate at room temperature (bottom pattern). The thermal analysis for this crystal solvate is set forth in FIG. 16.

Example 8

Preparation of Specific Crystal Forms

Example 8A

Preparation of epoB-TOβ

Preparation of Epothilone B Toluene Solvate

Epo B was dissolved in ~13 mL of ethyl acetate at ~40° C. One volume of toluene was added followed by concentration at a bath temp of <40° C. to 9 mL. This was reheated to ~55° C., followed by the addition of another volume of toluene. This was then concentrated to ~10 mL and allowed to cool to 18° C. The slurry was used for x-ray structure determination.

Figure 4:
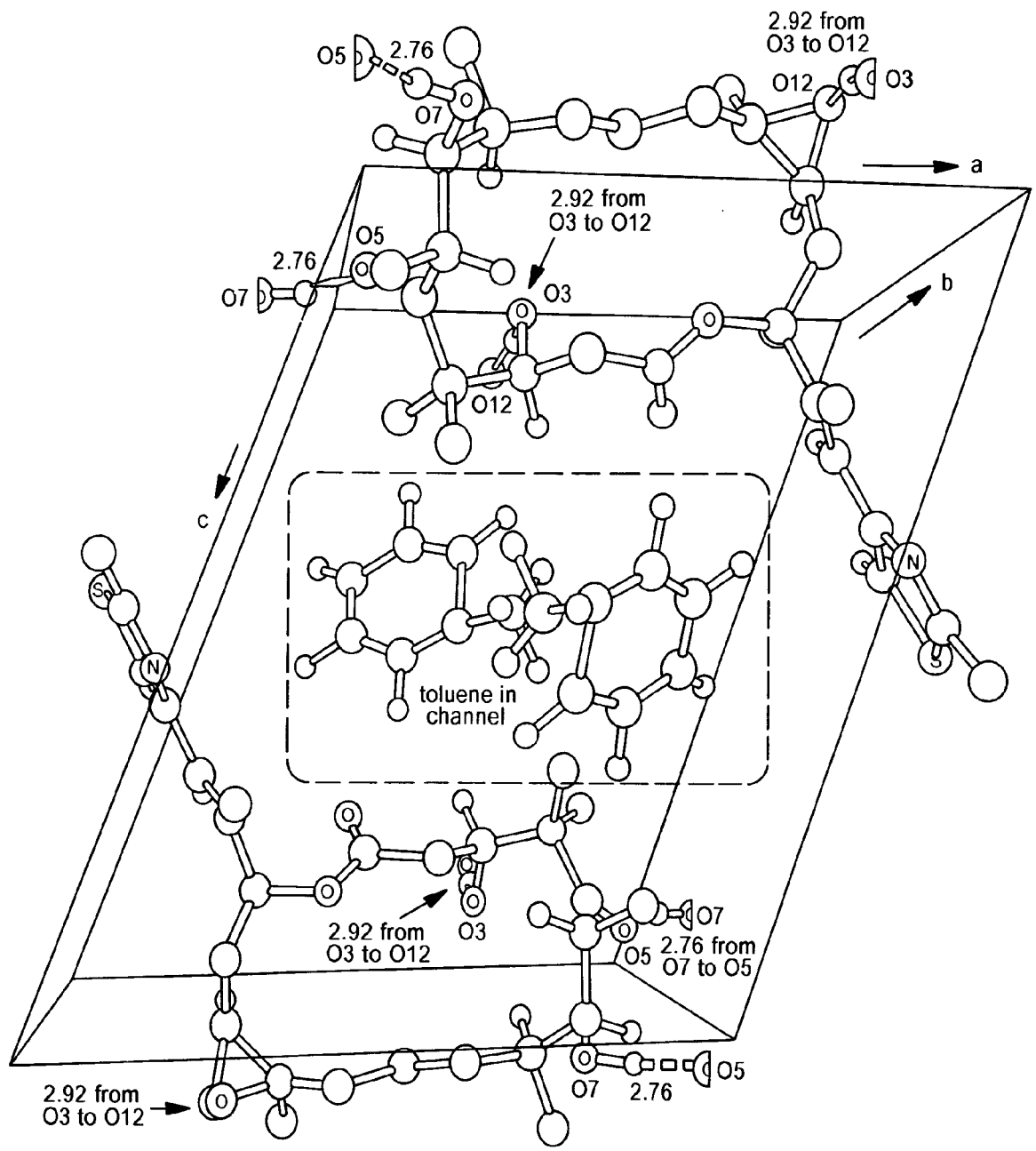
FIG. 4 shows the molecular structure in the monoclinic unit cell of form epoB-Toβ, with two molecules of epothilone B and two molecules of toluene in the guest channel of the monoclinic unit cell.
Figure 6:
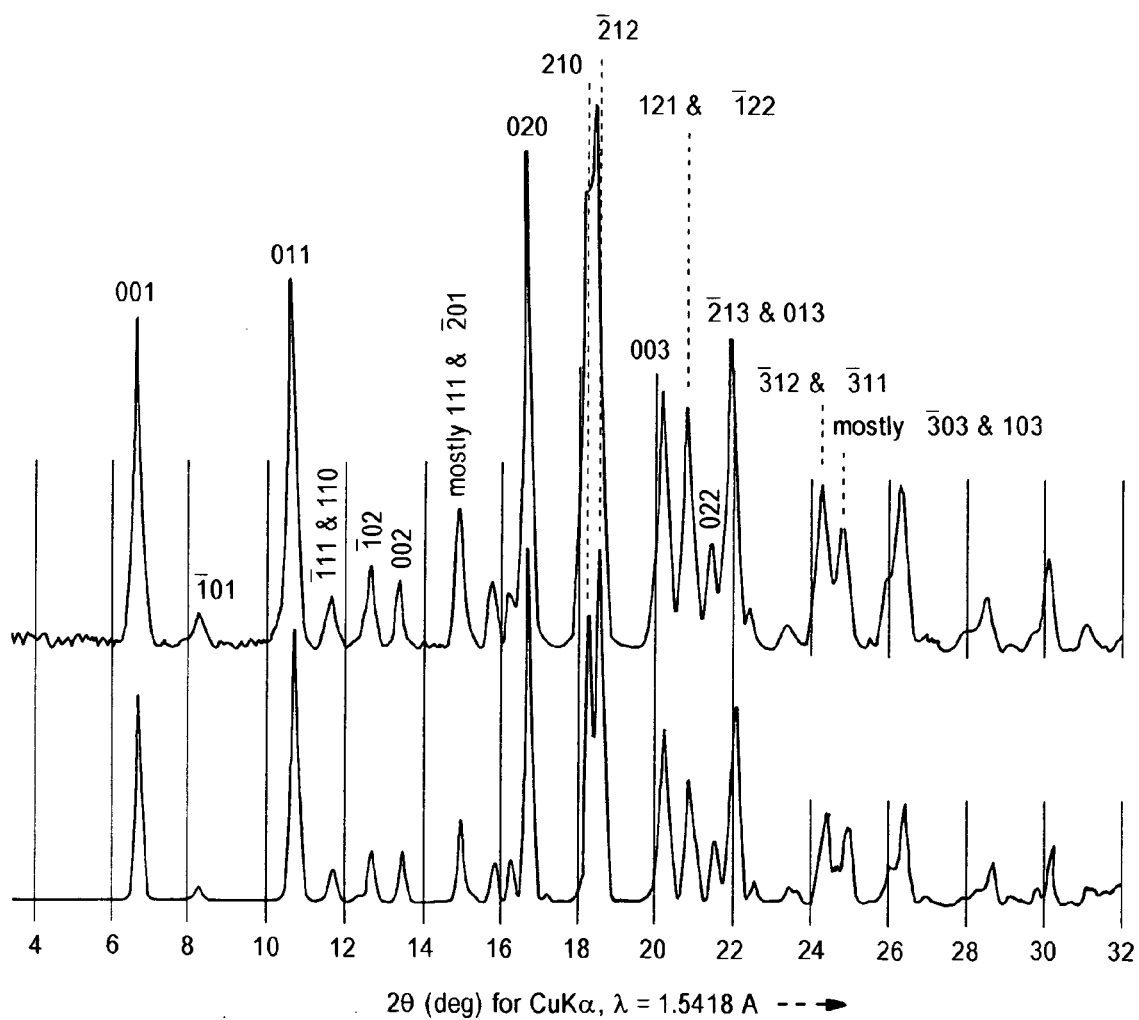
FIG. 6 shows observed (top) and simulated (bottom) PXRD patterns for the toluene solvate (crystal form epoB-TOβ) of epothilone B.

The molecular structure of the monoclinic unit cell form of epoB-TOβ and PXRD patterns of epoB-Toβ, obtained following the above-described method, are shown in FIGS. 4 and 6, respectively.

Example 8B

Preparation of epoB-ANβ

Preparation of Epothilone B Acetonitrile Solvate

A solution of essentially pure epothilone B in aqueous acetonitrile (from pooled column fractions resulting from the reverse phase chromatography in example 5) was allowed to evaporate slowly at room temperature to yield a crystal slurry from acetonitrile-water. The crystal slurry was examined directly by x-ray diffraction.

Figure 2:
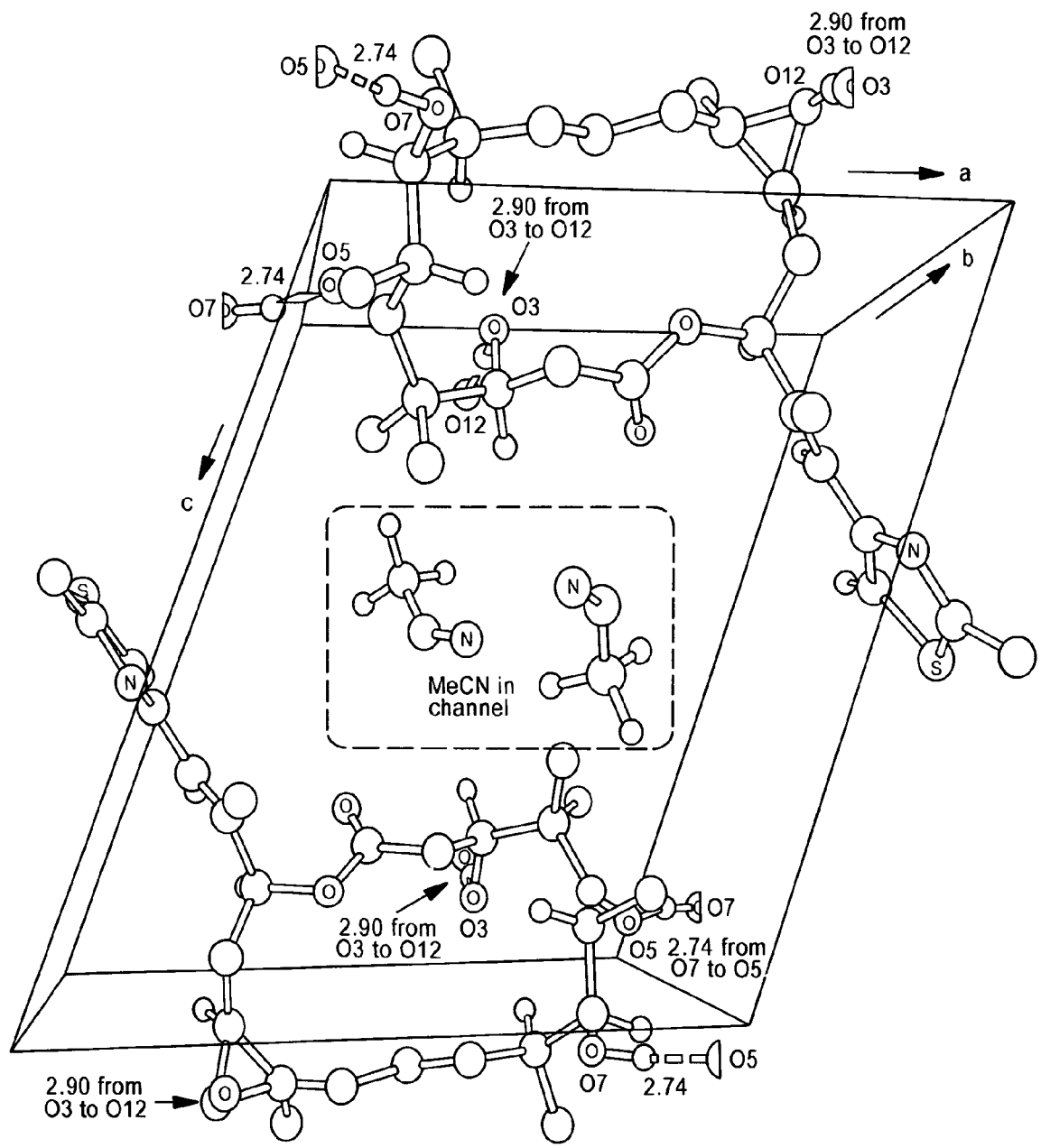
FIG. 2 shows the molecular structure in the monoclinic unit cell of form epoB-ANβ, with two molecules of epothilone B and two molecules of acetonitrile in the guest channel of the monoclinic unit cell.
Figure 7:
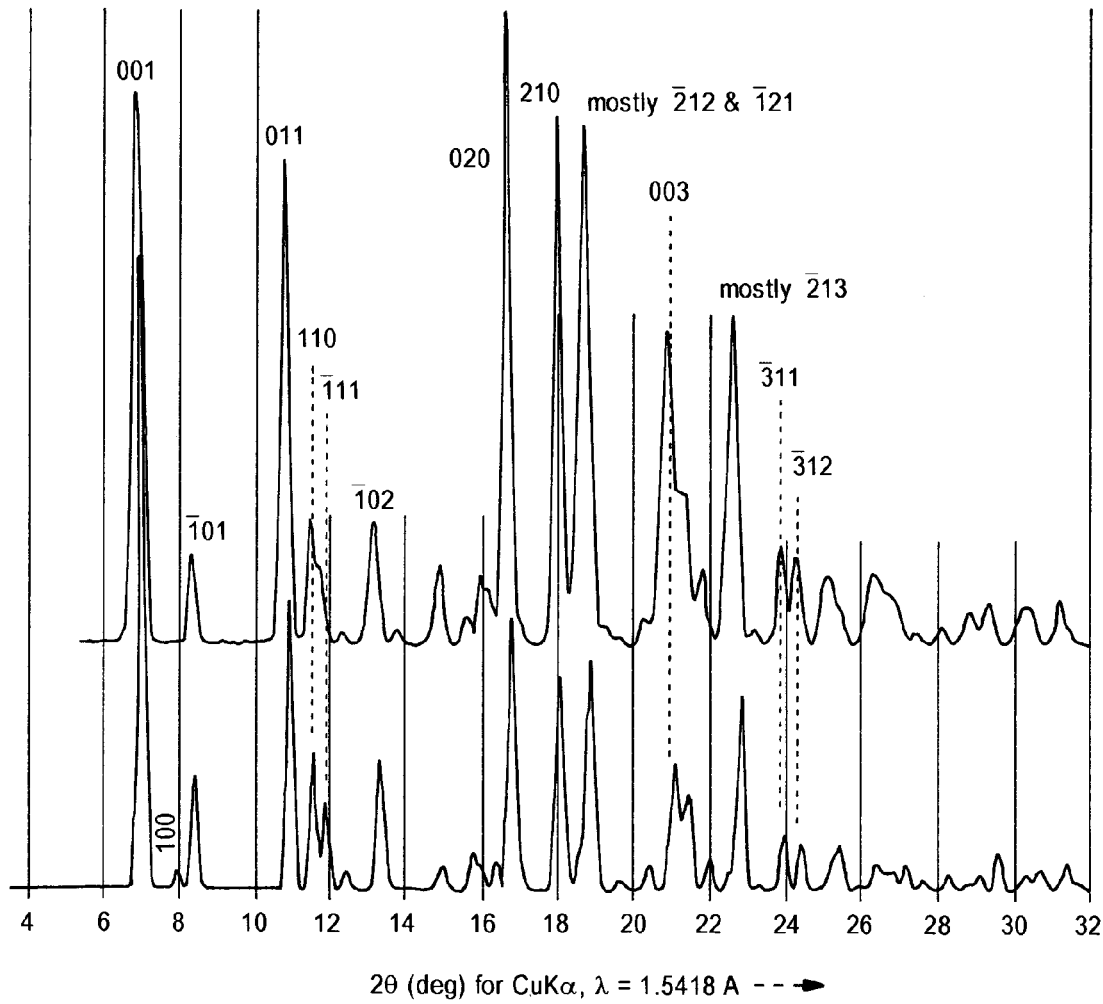
FIG. 7 shows observed (top) and simulated (bottom) PXRD patterns for the acetonitrile solvate (crystal form epoB-ANβ) of epothilone B.

The molecular structure of the monoclinic unit cell form of epoB-ANβ and the PXRD patterns of epoB-ANβ, obtained following the above-described method, are shown in FIGS. 2 and 7, respectively.

Example 8C

Preparation of epoB-EAβ

Preparation of Epothilone B EtOAc Solvate

A solution of epothilone B in 1:1 EtOAc/heptane is concentrated to a target concentration of ~190–195 g/L. To this thick slurry of epothilone B is added with stirring 10 volumes of EtOAc at ~40° C. The resulting slurry is stirred at 40° C. for 2 hours, is cooled to 0° C. over 5 hours and is further stirred at 0° C. for a minimum of 5 hours. The slurry is then filtered and the cake is washed with cold 1:1 EtOAc/heptane. The cake is dried in the vacuum oven for 5–6 hours to afford the final epothilone B cake with ~5–14% EtOAc.

Figure 5:
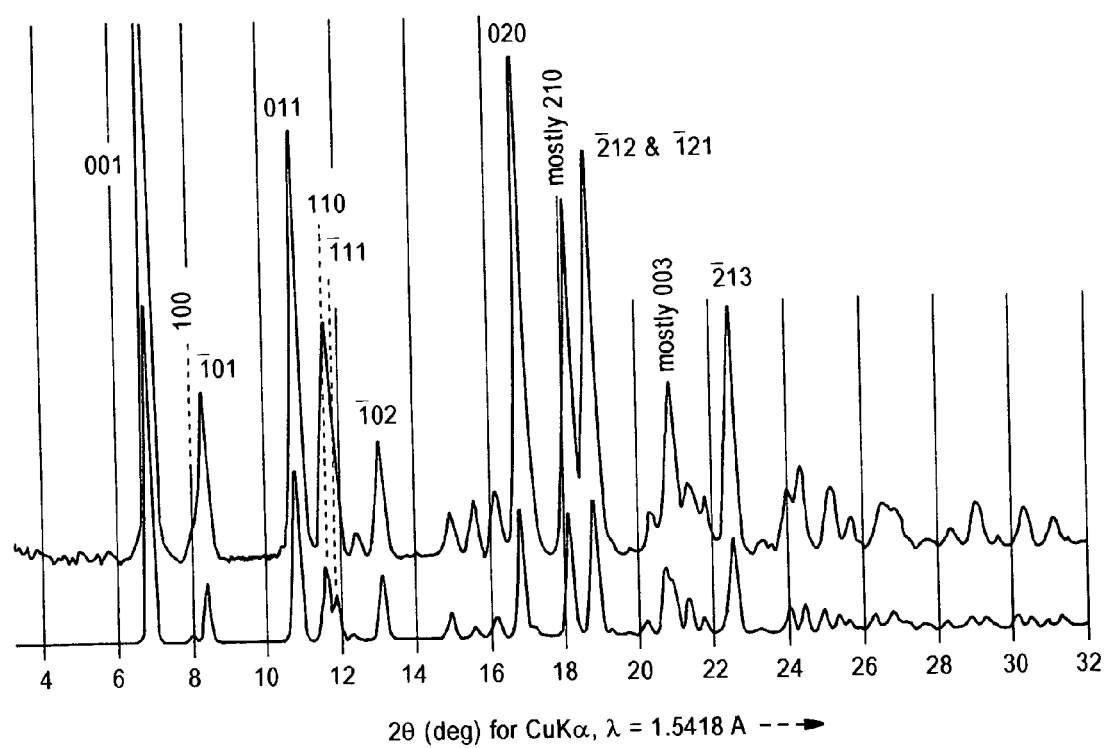
FIG. 5 shows observed (top) and simulated (bottom) PXRD patterns for the ethyl acetate solvate (crystal form epoB-EAβ) of epothilone B.

The molecular structure of the monoclinic unit cell form of epoB-EAβ and the PXRD patterns of epoB-EAβ, obtained following the above-described method, are shown in FIGS. 1 and 5, respectively.

Example 8D

Preparation of epoB-IPβ

Preparation of Epothilone B IPA Solvate

Epothilone B (70 mg) was dissolved in 4 mL of IPA by heating the solution until a clear solution was formed. This solution was cooled to ambient temperature. Any solids formed immediately were removed by filtration. The clear filtrate was placed in a small vial and covered with aluminum foil with a several pinholes. The solvent was allowed to evaporate at ambient temperature very slowly over a period of several days until substantial crystal growth was observed. Crystals were submitted for X-ray analysis as a wet slurry.

Figure 3:
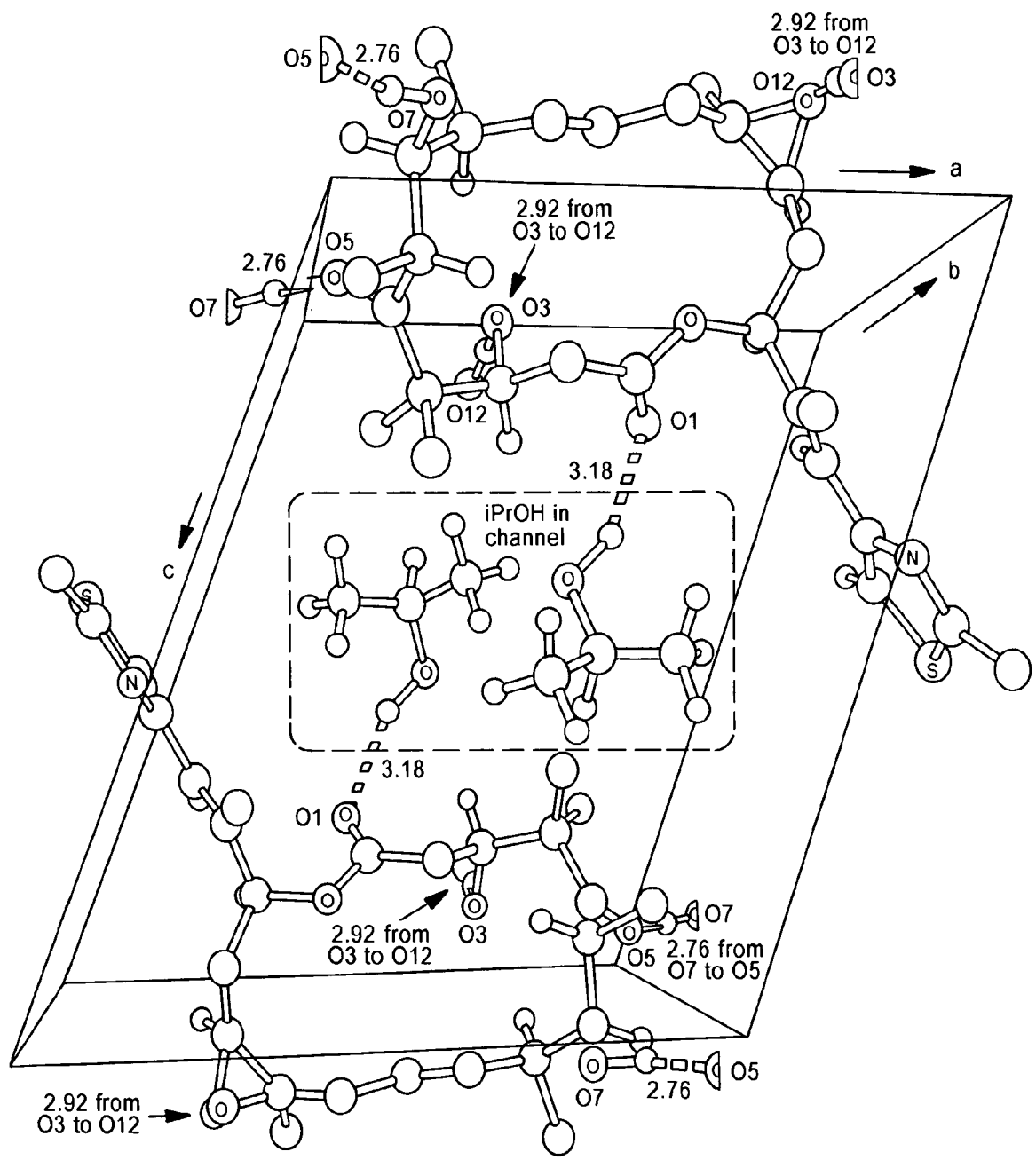
FIG. 3 shows the molecular structure in the monoclinic unit cell of form epoB-Ipβ, with two molecules of epothilone B and two molecules of isopropanol in the guest channel of the monoclinic unit cell.
Figure 8:
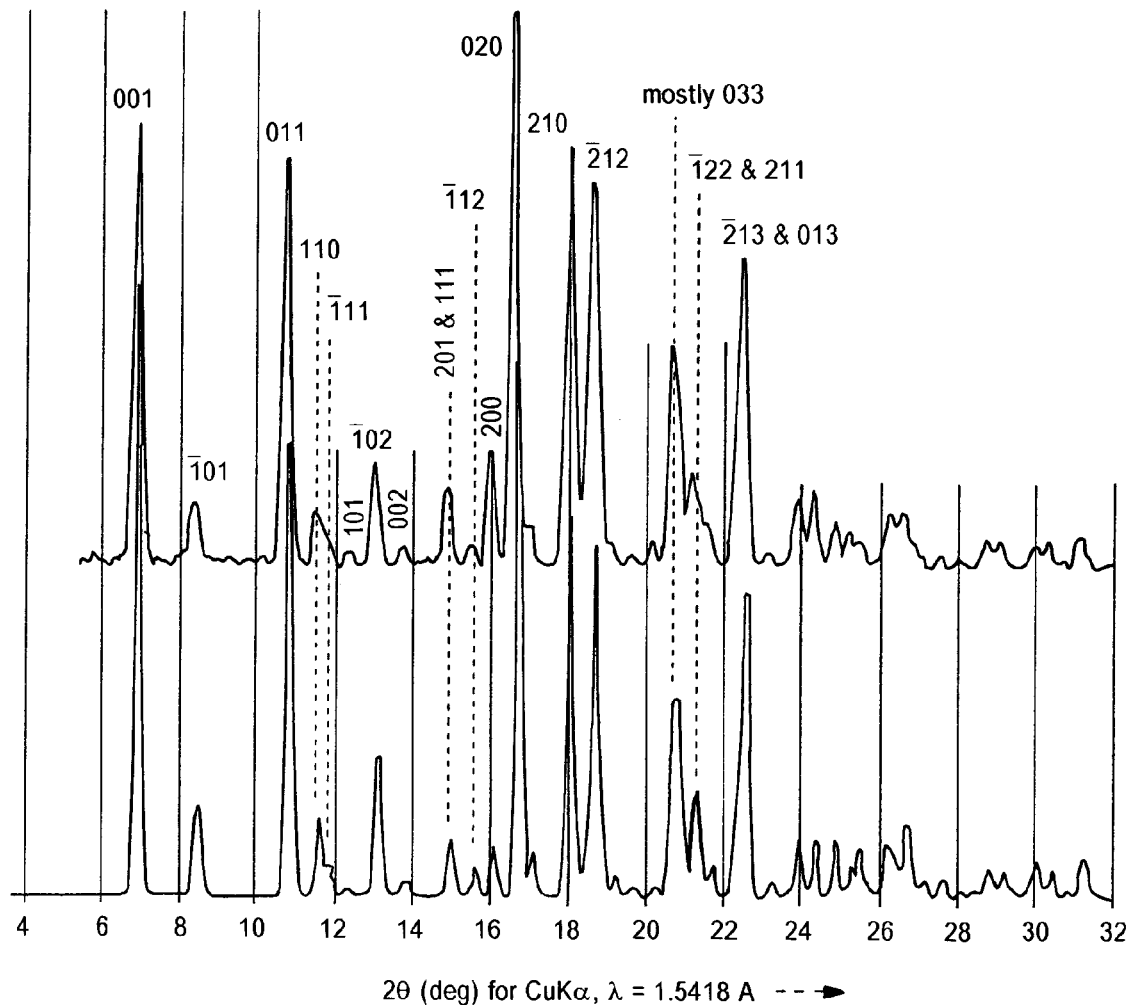
FIG. 8 shows observed (top) and simulated (bottom) PXRD patterns for the isopropyl alcohol solvate (crystal form epoB-IPβ) of epothilone B.

The molecular structure of the monoclinic unit cell form of epoB-IPβ and the PXRD patterns of epoB-IPβ, obtained following the above-described method, are shown in FIGS. 3 and 8, respectively.

Example 9

Forming Derivative 2 (a Lactam) from Epothilone B (a Lactone)

A tetrabutylammonium azide (TBA azide) solution is prepared by mixing tetrabutylammonium chloride and sodium azide in THF/DMF. The resulting TBA azide solution is recovered by removal of NaCl crystals by filtration. Catalytic amount of an agent such as tris(dibenzyledeneacetone)-dipalladium or the chlorofom adduct of this catalyst selected to stabilize an allylic cation, ammonium chloride, epothilone B, and the THF/DMF solution of TBA azide are charged into a flask with agitation. The slurry is deoxygenated by bubbling nitrogen for about 25 minutes at 0–5° C. Trimethylphospine is added at 0–5° C. The reaction mixture is heated to 32–38° C. and agitation is continued for 4–16 hours to produce an amino acid intermediate resulting from the breakage of the ester functionality. The reaction mixture is cooled to 18–24° C. and filtered to remove solids. The solids are washed with THF and the filtrate is combined with the rich filtrate. This solution is added dropwise over 9–10 hours to THF-DMF slurry of 1-hydroxybenzotriazole hydrate, 1-(3-dimethylaminopropyl)-3-ethylcarbodiimide hydrochloride, and potassium carbonate at 30–37° C. The resulting mixture is cooled to 0–12° C., quenched with water while keeping the temperature <10° C. The mixture is extracted with ethyl acetate three to four times, and the combined ethyl acetate layers are diluted with cyclohexane (3:1 ethyl acetate-cyclohexane ratio) and back extracted with water. The organic layer is further diluted to 2:1 ethyl acetate-cyclohexane ratio with additional cyclohexane and passed through an activated charcoal impregnated cartridge such as Zeta Pad R51SP or R53SP to reduce the amount of residual Pd. Triethylamine (1%) is added to the organic filtrate and the solution is purified by a short silica-gel filtration with 2:1 ethyl acetate-cyclohexane containing 1% triethylamine. Rich eluent is collected and concentrated at <37° C. to a final concentration of 11–14 mL/g. Additional cyclohexane is added and the slurry is heated at 67–78° C. for 45–60 minutes. The slurry is cooled slowly to about 21° C., filtered and the crystalline solid is washed with 1:1 ethyl acetate-cyclohexane. The wet cake is dried in vacuo at <45° C. to yield crystalline lactam analogue of epothilone B in about 56M% yield.

Example 10

Forming an Amino-Substituted Epothilone Derivative (Derivative 1) from Epothilone B Epothilone B is converted to epothilone F by enzymatic hydroxylation of the 2-methyl group on the thiazole ring of epothilone B. The conversion is achieved by the action of an actinomycete strain on epothilone B. Actinomycete strains for use in this step are disclosed in U.S. patent application Ser. No. 10/321,188, filed Dec. 17, 2002, and WO 00/39276, both of which are incorporated herein by reference.

Epothilone B in ethanol (5% v/w) is added to the microbe, grown in a suitable medium at 16–18° C., and the pH is maintained between 6.9 and 7.1 with either 50% w/v sodium hydroxide or 30% w/v sulfuric acid. Bioconversion is continued until the concentration of Epothilone B is reduced to 3–5% of its initial value. A resin such as XAD-16 or SP207 capable of adsorbing epothilone F is added to the fermentation tank (5% v/w) and stirred for 16–72 hours at 10–18° C. The fermentation broth is decanted and the resin is washed with water (2:1 water-resin ratio). The wash is repeated two more times. Most of the residual water is removed by filtration on a Buchner funnel.

XAD-16 resin, with pre-adsorbed epothilone F, is slurried with water and loaded onto a column. The resin columns are extracted with ethyl acetate and the rich eluate is collected. The aqueous layer is drawn off and the rich ethyl acetate fraction is then washed with a 5% sodium bicarbonate solution and water to remove color. The rich organic fraction is concentrated under reduced pressure, then passed through a filter precoated with silica, followed by a 10 µM polish filtration. The product is then distilled under vacuum and primary epothilone F is crystallized by adding toluene with stirring as an anti-solvent. The rich toluene mixture is further concentrated to reduce the ethyl acetate content and more toluene is added. The crystalline slurry is filtered and washed with toluene.

Epothilone F is dissolved in a methylene chloride or methylene chloride/ethyl acetate mixture, then loaded onto a chromatographic column packed with HPLC-grade silica that has been equilibrated with a 60–80:40–20 ethyl acetate:n-heptane mixture (v/v).

The product is eluted from the column with either an isocratic or step gradient of 60–80:40–20 ethyl acetate:n-heptane mixture (v/v), followed by 60–80:40–20 ethyl acetate:n-heptane mixture (v/v). The sample and process is monitored via UV detection at 290 nm. The epothilone F product peak is fractionated to minimize closely eluting impurities. Rich pooled fractions are distilled under vacuum to a target concentration of approximately 100 g/L. To the slurry of epothilone F, an equal volume of n-heptane is added with stirring. The batch is vacuum redistilled to a target concentration of approximately 100 g/L, ethyl acetate is added, and the slurry is maintained at 40° C. The batch is cooled to 2 to −10° C. and maintained for at least 5 hours at that temperature to crystallize the product from the solution. The resultant slurry is filtered and washed with cool 1:1 ethyl acetate/n-heptane solution. The final epothilone F cake is dried under vacuum at 35–40° C.

1,8-Diazabicyclo[5.4.0]undec-7-ene (DBU, 1.8 eq) is added slowly to a suspension of epothilone F and diphenylphosphoryl azide (1.5 eq) in tetrahydrofuran (previously dried over 3A MS) and the reaction is stirred at 15–25° C. for 12–24 hours. Trimethylphosphine/tetrahydrofuran solution (1.0 M, 1.1 eq) is slowly added to the reaction mixture. Water and ammonium hydroxide are added and the mixture is stirred for an additional 30 minutes. The reaction mixture is diluted with water and the aqueous phase is extracted with three portions of dichloromethane. The organic phase is then washed with diluted ammonium hydroxide and half-saturated sodium chloride solutions, and evaporated to dryness to afford the crude amino derivative (Derivative 1) functionalized on the thiazole methyl group.

The crude product is purified by column chromatography using silica gel pre-treated with 2.5% methanol-0.2% triethylamine-dichloromethane. The fractions of suitable quality are combined, microfiltered and evaporated to dryness to afford chromatographed Derivative 1. This material is added to ethyl acetate and the resulting suspension is heated at 72–75° C. to obtain a solution. Antisolvent n-heptane is added slowly and the mixture is allowed to cool slowly in the presence of seeds with stirring at 15–25° C. After cooling and holding at ~5° C., the resulting solid is isolated by filtration followed by vacuum drying to afford the purified crystalline amino derivative (Derivative 1) in about 70 M % average yield from Epothilone F.

Example 11

Preparation of Epothilone D (Derivative 3) from Epothilone B

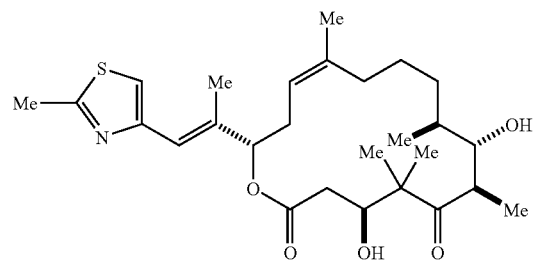

[4S-[4R*,7S*,8R*,9R*,15R*(E)]]-4,8-Dihydroxy-5,5,7,9,13-pentamethyl-16-[1-methyl-2-(2-methyl-4-thiazolyl)ethenyl]-1-oxa-13(Z)-cyclohexadecene-2,6-dione [Epothilone D, Derivative 3].

To anhydrous THF (5 ml) at −78° C. under argon was added $WCl_6$ (198 mg, 0.5 mmol) followed by nBuLi (0.625 ml of 1.6 M solution in hexanes, 1.0 mmol). The reaction was allowed to warm to room temperature over a 20 minute period. An aliquot (0.50 ml, 0.05 mmol) of the tungsten reagent was removed and added to epothilone B (9.0 mg, 0.018 mmol) under argon and the reaction mixture was stirred for 15 minutes, and then quenched by the addition of saturated $NaHCO_3$ (1 ml). The reaction mixture was extracted with EtOAc (3×1 ml), the combined extracts dried ($Na_2SO_4$), filtered, and the volatiles were removed under vacuum. The residue was chromatographed with 35% EtOAc/hexanes to give the title compound (7.0 mg, 0.014 mmol). MS m/z: 492.3 ($M^+$+H).

What is claimed is:

1. A crystalline solvate comprising: a toluene-containing epothilone B clathrate.

2. The crystalline solvate according to claim 1 characterized by unit cell parameters approximately equal to the following:

| | |
|---|---|
| Cell dimensions: | a = 11.853(1) Å |
| | b = 10.613(2) Å |
| | c = 14.328(2) Å |
| | Volume = 1659(1) Å$^3$ |
| Space group | P2$_1$ |
| Molecules/unit cell | 4 |
| Density (calculated) (g/cm$^3$) | 1.201 | wherein the crystalline solvate is at a temperature of about −33° C.

3. The crystalline solvate according to claim 1 wherein said crystalline solvate is characterized by peaks in a powder x-diffraction pattern at a value of two theta (CuKα λ=1.5418 Å) of about 13.4, 20.2, 22.0, and 24.9, at a temperature of 23° C.

4. The crystalline solvate according to claim 3 wherein said crystalline solvate is further characterized by peaks in a powder x-ray diffraction pattern at a value of two theta (CuKα λ=1.5418 Å)of about 6.7, 8.2, 11.7, 12.7, 15.0, 15.8, 16.7, 18.5, 20.9, 21.5, 24.3, 26.3, 28.5, and 30.1, at a temperature of 23° C.

5. The crystalline solvate according to claim 1, which comprises about one molecule of toluene per one molecule of the epothilone B.

6. The crystalline solvate according to claim 5 characterized by unit cell parameters approximately equal to the following:

| | |
|---|---|
| Cell dimensions: | a = 11.853(1) Å |
| | b = 10.613(2) Å |
| | c = 14.328(2) Å |
| | Volume = 1659(1) Å$^3$ |
| Space group | P2$_1$ |
| Molecules/unit cell | 4 |
| Density (calculated) (g/cm$^3$) | 1.201 | wherein the crystalline solvate is at a temperature of about −33° C.

7. The crystalline solvate according to claim 5 wherein said crystalline solvate is characterized by peaks in a powder x-diffraction pattern at a value of two theta (CuKα λ=1.5418 Å) of about 13.4, 20.2, 22.0, and 24.9, at a temperature of 23° C.

8. The crystalline solvate according to claim 7 wherein said crystalline solvate is further characterized by peaks in a powder x-ray diffraction pattern at a value of two theta (CuKα λ=1.5418 Å) of about 6.7, 8.2, 11.7, 12.7, 15.0, 15.8, 16.7, 18.5, 20.9, 21.5, 24.3, 26.3, 28.5, and 30.1, at a temperature of 23° C.

9. The crystalline solvate according to claim 1 characterized by: fractional atomic coordinates substantially as listed in Table 5.

* * * * *

UNITED STATES PATENT AND TRADEMARK OFFICE
CERTIFICATE OF CORRECTION

PATENT NO. : 7,241,899 B2 Page 1 of 1
APPLICATION NO. : 10/805724
DATED : July 10, 2007
INVENTOR(S) : Daniel A. Benigni et al.

It is certified that error appears in the above-identified patent and that said Letters Patent is hereby corrected as shown below:

Claim 2, Col. 35, line 8, change "4" to read -- 2 --.

Claim 6, Col. 36, line 8, change "4" to read -- 2 --.

Signed and Sealed this

Eighteenth Day of March, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,241,899 B2 | Page 1 of 1 |
| APPLICATION NO. | : 10/805724 | |
| DATED | : July 10, 2007 | |
| INVENTOR(S) | : Benigni et al. | |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 169 days Delete the phrase "by 169 days" and insert -- by 308 days --

Signed and Sealed this

Second Day of September, 2008

JON W. DUDAS
*Director of the United States Patent and Trademark Office*